United States Patent [19]
Babin et al.

[11] Patent Number: 5,180,741
[45] Date of Patent: Jan. 19, 1993

[54] PYRETHRINOID ESTERS CARRYING AN INDANYL NUCLEUS AND THEIR USE AS PESTICIDES

[75] Inventors: Didier Babin, Montigny; Jean-Pierre Demoute, Auriol; Jean Tessier, Vincennes, all of France

[73] Assignee: Roussel Uclaf, Paris, France

[21] Appl. No.: 713,697

[22] Filed: Jun. 11, 1991

Related U.S. Application Data

[63] Continuation of Ser. No. 432,732, Oct. 13, 1989, abandoned.

[30] Foreign Application Priority Data

Mar. 3, 1988 [FR] France ............... 89 00087

[51] Int. Cl.$^5$ ............... A01N 37/08; C07C 61/06
[52] U.S. Cl. ............... 514/531; 514/460; 514/463; 549/420; 549/454; 560/124
[58] Field of Search ............... 560/124; 514/531, 460, 514/463; 549/420, 454

[56] References Cited

U.S. PATENT DOCUMENTS 3,647,857 3/1972 Morgan ............... 560/124

FOREIGN PATENT DOCUMENTS 0215701 3/1987 European Pat. Off. .

Primary Examiner—Joseph Paul Brust
Assistant Examiner—Jacqueline Haley
Attorney, Agent, or Firm—Bierman and Muserlian

[57] ABSTRACT

Pyrenthrinoid esters with an indenyl nucleus having the following structural formula

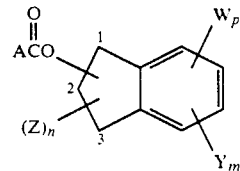

wherein the substituents are herein defined, have been shown to be useful as pesticides and in pesticidal compositions.

10 Claims, No Drawings

PYRETHRINOID ESTERS CARRYING AN INDANYL NUCLEUS AND THEIR USE AS PESTICIDES

This is a continuation of Ser. No. 432,732 filed Oct. 13, 1989, now abandoned.

The present invention relates to new pyrethrinoid esters carrying an indanyl nucleus, their preparation process and their use as pesticides.

A subject of the invention is, in all the possible isomer forms, as well as their mixtures, the compounds of formula (I):

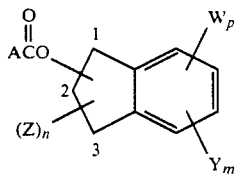
(I)

in which the radical

is fixed in position 1 or 2, A representing the radical:

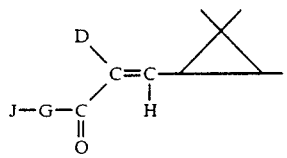

in which D represents a hydrogen or halogen atom, an alkoxy radical containing 1 to 8 carbon atoms, G represents an oxygen or sulphur atom and J represents either a saturated or unsaturated linear, branched or cyclic alkyl radical containing 1 to 8 carbon atoms, optionally substituted by one or more identical or different functional groups, or an aryl group containing 6 to 14 carbon atoms, optionally substituted by one or more identical or different functional groups, or a heterocyclic radical optionally substituted by one or more identical or different functional groups.

Z in position 1, 2 or 3 represents a hydrogen atom, a halogen atom, a saturated or unsaturated linear, branched or cyclic alkyl radical containing up to 8 carbon atoms, an aryl radical containing up to 14 carbon atoms or a keto group, n representing the number 1, 2 or 3;

Y in any position on the aromatic nucleus represents a hydrogen atom, a halogen atom, a $CF_3$ radical, a CN radical, an optionally substituted aryl radical containing up to 14 carbon atoms, a saturated or unsaturated linear, branched or cyclic alkyl radical containing up to 8 carbon atoms, optionally substituted by one or more halogen atoms, by a CN,

$CO_2R_2$ or $OR_3$ radical, $R_1$, $R_2$ and $R_3$ representing a saturated or unsaturated linear, branched or cyclic alkyl radical containing up to 8 carbon atoms, an optionally substituted aryl radical containing up to 14 carbon atoms, m representing 1 or 2;

W in any position on the phenyl nucleus, representing either one of the values indicated above for Y, or an $NO_2$, $OCH_3$, $N_3$, $N(R_4)_2$ or $SnR_5$ radical, $R_4$ and $R_5$ representing a hydrogen atom or a saturated or unsaturated linear, branched or cyclic alkyl radical containing up to 8 carbon atoms, p representing 1 or 2, provided that if Z and W represent a hydrogen atom, if the radical

is in position 2 and if n represents 1, Y does not represent a phenyl radical in position 4.

When Z, Y or W represents a halogen atom, it is preferably a fluorine, chlorine or bromine atom.

When Z, Y, W, $R_1$, $R_2$, $R_3$, $R_4$ or $R_5$ represents a saturated linear or branched alkyl radical, it is preferably one of the following radicals: methyl, ethyl, n-propyl, isopropyl, n-butyl, sec-butyl, isobutyl, n-pentyl, n-hexyl, tert-butyl or tert-pentyl or neo-pentyl.

When Z, Y, W, $R_1$, $R_2$, $R_3$, $R_4$ or $R_5$ represents an unsaturated alkyl radical, it is preferably an ethylene radical such as, for example, a vinyl, allyl, 1,1-dimethylallyl or 2-butenyl radical or an acetylene radical such as, for example, an ethynyl or propynyl radical.

When Z, Y, W, $R_1$, $R_2$, $R_3$, $R_4$ or $R_5$ represents a cyclic alkyl radical, it is preferably a cyclopropyl, cyclobutyl, cyclopentyl or cyclohexyl radical.

When Z, Y, W, $R_1$, $R_2$ or $R_3$ represent an aryl radical, it is preferably a phenyl radical.

When D represents a halogen atom, it is preferably a fluorine, chlorine or bromine atom.

When J represents an alkyl radical substituted by one or more functional groups, by alkyl is preferably understood a radical containing 1 to 8 carbon atoms such as, for example, one of the following radicals: methyl, ethyl, propyl, isopropyl, n-butyl, isobutyl or tert-butyl and by functional group, one of those mentioned in the European Application published under the No. 50534.

J can also represent an alkyl radical substituted by an aryl radical, in particular by an optionally substituted phenyl radical.

When J represents an alkyl radical substituted by one or more functional groups, there can be cited as preferred values of J, the radicals: $-(CH_2)_{n1}-C(Hal)_3$ in which $n_1$ is an integer from 1 to 8, and Hal is a halogen atom, for example the radical $-CH_2-CCl_3$, $-CH_2-CF_3$, $-CH_2-CH_2-CCl_3$ or $-CH_2-CH_2-CF_3$; $-(CH_2)_{n2}-CH(Hal)_2$ in which Hal is defined as above and $n_2$ is a number from 0 to 8, for example the radical $-CH_2-CHCl_2$, $-CH_2-CHF_2$ or $-CHF_2$; $-(CH_2)_{n1}-CH_2(Hal)$ in which $n_1$ and Hal are defined as above, for example the radical $-CH_2-CH_2Cl$ or $-CH_2-CH_2F$; $-C[C(Hal)_3]_3$ in which Hal is defined as above, for example the radical

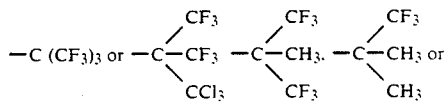

-continued $$\underset{CH_2-CH_3}{\overset{CF_3}{C-CH_3}} \quad -\underset{H}{\overset{CF_3}{C-CH_3}}, \text{ or } -\underset{H}{\overset{CF_3}{C-CF_3}} \quad -\underset{CH_3}{\overset{CH_3}{C-CN}}, \quad -\underset{H}{\overset{CH_3}{C-CN}} \text{ or}$$

$$-(CH_2)_n-CN,$$

in which n is defined as previously, $$-\underset{H}{\overset{C(Hal)_3}{C-CN}}$$

in which Hal is defined as previously, for example the radical $$-\underset{H}{\overset{CCl_3}{C-CN}}.$$

—$(CH_2)_{n1}$—$OR_a$, in which $n_1$ is defined as previously and $R_a$ represents a hydrogen atom or a linear or branched alkyl radical containing 1 to 8 carbon atoms, for example the radical —$CH_2$—$OCH_3$, —$CH_2$—$CH_2$—$O$—$CH_3$, —$CH_2$—$CH_2$—$O$—$CH_2$—$CH_3$ or —$CH_2$—$CH_2$—$OH$;

$$-(CH_2)_{n1}-N\overset{R_a}{\underset{R_a}{\diagdown}}$$

in which $n_1$ and $R_a$ are defined as previously and the two radicals $R_a$ can be different from each other, for example the radical $$-CH_2-CH_2-N\overset{CH_3}{\underset{H}{\diagdown}}, \quad -CH_2-CH_2-N\overset{CH_3}{\underset{CH_3}{\diagdown}} \text{ or}$$

$$-CH_2-CH_2-N\overset{CH_3}{\underset{CH_2-CH_3}{\diagdown}}; \quad -(CH_2)_{n1}-\underset{O}{\overset{CH}{\underset{|}{\phantom{X}}}}\underset{O}{\overset{CH_2}{\underset{|}{\phantom{X}}}}$$
$$H_3C\overset{\phantom{X}}{\diagup}\overset{\phantom{X}}{\diagdown}CH_3$$

in which $n_1$ is defined as previously, for example the radical $$-CH_2-\underset{O}{\overset{CH}{\underset{|}{\phantom{X}}}}\underset{O}{\overset{CH_2}{\underset{|}{\phantom{X}}}}; \quad -(CH_2)_{n1}-\underset{OH}{\overset{CH}{\underset{|}{\phantom{X}}}}\underset{OH}{\overset{CH_2}{\underset{|}{\phantom{X}}}}$$
$$H_3C\overset{\phantom{X}}{\diagup}\overset{\phantom{X}}{\diagdown}CH_3$$

in which $n_1$ is defined as previously, for example the radical $$-CH_2-\underset{OH}{\overset{CH}{\underset{|}{\phantom{X}}}}-CH_2-OH; \quad -(CH_2)_{n1}-O\underset{\phantom{X}}{\diagup}\overset{O}{\diagdown}$$

in which $n_1$ is defined as previously, for example the radical $$-(CH_2)-O\underset{\phantom{X}}{\diagup}\overset{O}{\diagdown} \text{ or } -CH_2-CH_2-O\underset{\phantom{X}}{\diagup}\overset{O}{\diagdown};$$

$$-(CH_2)_{n1}-\underset{\phantom{X}}{\diagup}\overset{\phantom{X}}{\diagdown}.$$

in which $n_1$ is defined as previously, for example the radical benzyl or phenethyl;

$$-(CH_2)_{n1}-\underset{\phantom{X}}{\diagup}\overset{\phantom{X}}{\diagdown}.$$

in which $n_1$ is defined as previously, for example the radical $$-CH_2-\underset{\phantom{X}}{\diagup}\overset{O}{\underset{O}{\diagdown}}$$

When J represents an optionally substituted aryl radical, it is preferably an optionally substituted phenyl radical.

When J represents a heterocyclic radical, it is preferably one of the following radicals: pyridyl, furyl, thienyl, oxazolyl or thiazolyl.

Among the preferred compounds of the invention, there can be cited the compounds of formula (I) in which D represents a hydrogen or fluorine atom, G represents an oxygen atom and J represents a saturated or unsaturated linear, branched or cyclic alkyl radical containing up to 4 carbon atoms, optionally substituted by one or more halogen atoms.

Among the preferred compounds of the invention, there can also be cited the compounds in which Z represents a hydrogen or fluorine atom, and those in which W represents a hydrogen atom. There can also be cited the compounds in which the radical $$\underset{A-C-O}{\overset{O}{\parallel}}$$

is in position 1 or also those in which Y is in position 4 and m represents the number 1.

Among the preferred compounds, in addition there can be cited the compounds in which Y represents a bromine atom, a —C≡N group, —$CH_2$—$CH$=$CH_2$, —$CH_2$—C≡CH, —$CH_2$—C≡CN and quite particularly the compounds in which Y represents the radical —$CH_2$C≡CH.

Among the preferred compounds of the invention, there can naturally be cited the compounds of which the preparation is given hereafter in the experimental part, and in particular the compounds of Examples 1, 2, 5, 6, 7, 32, 35, 54, 56 and 57.

The compounds of formula (I) offer useful properties which enable them to be used for combating parasites; for example for combating parasites of vegetation, parasites of premises and parasites of warm-blooded animals. It is in this way that the products of the invention can be used for combating parasitic insects, nematodes and acarids of vegetation and of animals.

A subject of the invention is therefore the use of the compounds of formula (I) for combating parasites of vegetation, parasites of premises and parasites of warm-blooded animals.

The products of formula (I) can therefore be used in particular for combating insects in the agricultural domain, for example for combating aphids, and larvae of lepidoptera and coleoptera. They are used at doses of between 1 g and 300 g of active material per hectare.

The products of formula (I) can also be used for combating insects in premises, for combating in particular flies, mosquitoes and cockroaches.

Among the preferred products of the invention, there can be cited those of Examples 1, 2, 5, 6, 7, 32, 35, 54, 56 and 57.

The products of formula (I) can also be used for combating parasitic acarids of vegetation.

The compounds of formula (I) can also be used for combating parasitic nematodes of vegetation.

The compounds of formula (I) can also be used for combating parasitic acarids of animals, for example for combating ticks and in particular ticks of Boophilus species, those of Hyalomnia species, those of Amblyomnia species and those of Rhipicephalus species, or for combating all types of mites, and notably the sarcoptic mite, the psoroptic mite and the chorioptic mite.

Also a subject of the invention is therefore the compositions intended for combating parasites of warm-blooded animals, parasites of premises and of vegetation, characterized in that they contain at least one of the products defined above.

In particular a subject of the invention is insecticide compositions containing as active principle at least one of the products defined above.

The compositions according to the invention are prepared according to the usual processes of the agrochemical industry or the veterinary industry, or of the industry of products intended for animal nutrition.

These compositions can be presented in the form of powders, granules, suspensions, emulsions, solutions, aerosol solutions, combustible bands, baits or other preparations traditionally employed for the use of these types of compounds.

In addition to the active principle, these compositions contain, in general, a vehicle and/or a non-ionic surface active agent, furthermore ensuring a uniform dispersion of the constitutive substances of the mixture. The vehicle used can be a liquid, such as water, alcohol, hydrocarbons or other organic solvents, a mineral, animal or vegetable oil, a powder such as talc, clays, silicates, kieselguhr, or a combustible solid.

The insecticide compositions according to the invention preferably contain from 0.005% to 10% by weight of active material.

According to an advantageous operating method, for use in premises, the compositions according to the invention are used in the form of fumigant compositions.

The compositions according to the invention can then advantageously be constituted, for the inactive part, of a combustible insecticide serpentine (or coil), or also an incombustible fibrous substrate. In this latter case, the fumigant obtained after incorporation of the active material is placed on a heating apparatus such as an electromosquito destroyer.

When an insecticide serpentine is used, the inert support can be, for example, composed of pyrethrum marc, Tabu powder (or Machilus Thumbergii leaf powder), pyrethrum stem powder, cedar leaf powder, sawdust (such as pine sawdust), starch and coconut shell powder. The dose of active material can then be, for example, 0.03 to 1% by weight.

When an incombustible fibrous support is used, the dose of active material can then be, for example, 0.03 to 95% by weight.

The compositions according to the invention for use in premises can also be obtained by preparing a sprayable oil based on the active principle, this oil soaking the wick of a lamp and then being set alight.

The concentration of active principle incorporated in the oil is preferably 0.03 to 95% by weight.

A subject of the invention is also acaricide compositions containing as active principle at least one of the products of formula (I) defined above.

A subject of the invention is also nematocide compositions containing as active principle at least one of the products of formula (I) above.

The insecticide compositions according to the invention, like the acaricide and nematocide compositions, can optionally have added to them one or more other pesticide agents. The acaricide and nematocide compositions can be presented in particular in the form of powder, granules, suspensions, emulsions, or solutions.

For acaricide use, wettable powders are preferably used for foliar spraying, containing 1 to 80% of active principle, or liquids for foliar spraying, containing 1 to 500 g/liter of active principle. Powders can also be used for foliar dusting, containing 0.05 to 3% of active material.

For nematocide use, liquids are preferably used for soil treatment, containing 300 to 500 g/liter of active principle.

The acaricide and nematocide compounds according to the invention are preferably used at doses of between 1 and 100 g of active material per hectare.

A subject of the invention is also acaricide compositions intended for combating parasitic acarids of warm-blooded animals, notably against ticks and mites, characterized in that they contain as active principle, at least one of the products of formula (I) defined above.

To enhance the biological activity of the products of the invention, they can have added to them synergists traditionally used in such a case such as 1-(2,5,8-trioxadodecyl)-2-propyl-4,5-methylenedioxy benzene (or piperonyl butoxide), or N-(2-ethyl heptyl)-bicyclo-[2.2-1]-hept-5-en-2,3-dicarboximide, or piperonyl-bis-[2-(2'-n-butoxyethoxy)ethyl]-acetal (or tropital).

When combating parasitic acarids of animals, very often the products of the invention are incorporated in food compositions in combination with a nutritive mixture suitable for animal fodder. The nutritive mixture can vary according to the type of animal, it can contain cereals, sugars and grains, soya, peanut and sunflower cakes, flours of animal origin, for example fish meal, synthetic amino acids, mineral salts, vitamins and antioxidants.

Therefore a subject of the invention is also the compositions intended for animal fodder, containing as active principle at least one of the products of formula (I) as defined previously.

It can also be pointed out that the products of the invention can be used as biocides or as growth regulators.

Also a subject of the invention is the combinations endowed with insecticide, acaricide or nematocide activity, characterized in that they contain as active material, on the one hand at least one of the compounds of general formula (I), and on the other hand, at least one of the pyrethrinoid esters chosen from the group constituted by the esters of allethrolone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohols with chrysanthemic acids, by the esters of 5-benzyl-3-furyl methyl alcohol with 2,2-dimethyl-3-(2-oxo-3,4,5,6,-tetrahydrothiophenylidenemethyl) cyclopropanecarboxylic acids, by the esters of 3-phenoxybenzyl alcohol and of alpha-cyano-3-phenoxybenzyl alcohols with 2,2-dimethyl-3-(2,2-dichlorovinyl)cyclopropanecarboxylic acids, by the esters of alpha-cyano-3-phenoxy-benzyl alcohols with 2,2-dimethyl-3-(2,2-dibromovinyl)cyclopropanecarboxylic acids, by the esters of 3-phenoxybenzyl alcohol with 2-parachlorophenyl-2-isopropyl acetic acids, by the esters of allethrolones, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohols with 2,2-dimethyl-3-(1,2,2,2-tetrahaloethyl)cyclopropanecarboxylic acids, in which "halo" represents a fluorine, chlorine or bromine atom, it being understood that the compounds (I) can exist in all their possible stereoisomer forms, as well as the acid and alcohol copulas of the above pyrethrinoid esters.

The combinations according to the invention have in particular the value of enabling, by the polyvalency of their action, a more extensive range of parasites to be combated, and also in some cases of showing a synergic effect.

A subject of the invention is the pesticide compositions defined previously, characterized in that they contain in addition a pyrethrinoid synergist.

As standard synergists used in such a case, there can be cited 1-(2,5,8-trioxadodecyl)-2-propyl-4,5-methylenedioxy benzene (or piperonyl butoxide), or N-(2-ethylheptyl)-bicyclo-[2,2-1]-hept-5-en-2,3-dicarboximide, or piperonal-bis-[2-(2'-n-butoxy-ethoxy)ethyl]acetal (or tropital).

A subject of the invention is also a process for the preparation of compounds of formula (I), characterized in that an acid of formula (II):

$$\underset{\text{ACOH}}{\overset{\text{O}}{\|}} \quad (II)$$

in which A is defined as previously, or a functional derivative of this acid, is submitted to the action of an alcohol of formula (III):

(III)

[structure: indane with HO, $(Z)_n$, $W_p$, $Y_m$ substituents]

in which W, Y, Z, m, n and p are defined as previously, so as to obtain the corresponding compound of formula (I).

The compounds of formula (III) in racemic form are compounds known in a general way, described or considered in Agr. Biol. Chem. 1978, 42, 1365.

The compounds of formula (III) in resolved form are new and can be prepared by enzymatic hydrolysis of the corresponding esters. In order to carry out the enzymatic hydrolysis, a lipase can be used, for example the lipase from the pancreas of a pig, as will be indicated hereafter in the experimental part.

The compounds of formula (III) in resolved form are themselves a subject of the present invention.

Some products of formula (III) in racemic form are new and are themselves one of the subjects of the present invention. Their preparation is given hereafter in the experimental part.

The following examples illustrate the invention without however limiting it.

EXAMPLE 1

4-(2-propenyl)-1-indanyl [1R-[1-alpha(RS*),3-alpha(Z)]]-3-[3-(1,1-dimethylethoxy)-3-oxo-1-propenyl]-2,2-dimethylcyclopropanecarboxylate 0.58 g of [1Rcis (Z)]-2,2-dimethyl-(1,1-dimethylethoxy)-3-oxo-1-propenylcyclopropanecarboxylic acid, 6 ml of methylene chloride, 0.42 g of (RS) 4-(2-propenyl)-1-indanol and 50 mg of 4-dimethylamino pyridine are mixed together and cooled to 0° C. Drop by drop 0.51 g of dicyclohexylcarbodiimide in 1.5 ml of methylene chloride is added and agitation is carried out for 17 hours at ambient temperature. The urea formed is filtered and the filtrate is concentrated to dryness under reduced pressure. The residue is chromatographed on silica, eluting with a hexane-isopropyl ether mixture (9-1), and 0.43 g of impure product and 0.46 g of expected pure product are separated off. After chromatography on silica, the impure fraction is purified, by eluting with a hexane-isopropyl ether mixture (9.5-0.5) and a further 0.34 g of pure product is recovered.

$[alpha]_D = +53.5° \pm 2.5°$ c=0.4% CHCl$_3$

The alcohol used at the start is prepared according to the process described in Agr. Biol. Chem. 1978 42 1365.

EXAMPLE 2

4-(2-propenyl)-1-indanyl [1R-[1-alpha(RS*),3-alpha(E)]]-3-(2-fluoro-3-ethoxy-3-oxo-1-propenyl)-2,2-dimethylcyclopropanecarboxylate $[alpha]_D = +20.7° \pm 2°$ c=0.4% CHCl$_3$

EXAMPLE 3

4-(2-propenyl)-2-indanyl [1R-[1-alpha(RS*),3-alpha(E)]]-3-(3-ethoxy-2-fluoro-3-oxo-1-propenyl)-2,2-dimethylcyclopropanecarboxylate $[alpha]_D = +19.5° \pm 1°$ c=1% CHCl$_3$

EXAMPLE 4

4-(2-propenyl)-2-indanyl [1R-[1-alpha(RS*),3-alpha(Z)]]-3-[3-(1,1-dimethylethoxy)-3-oxo-1-propenyl]-2,2-dimethylcyclopropanecarboxylate

| NMR Spectrum CDCl₃ ppm: | |
|---|---|
| 1.23-1.3 | H of the twinned methyls |
| 1.48 | H of the tert-butyl |
| 1.78-1.93 | H in position 1 of the cyclopropane cycle |
| 4.78-5.2 | H in position 3 of the 2-propenyl group |
| 2.7-3.5 | H₃ of the cyclopropyl and H of the —CH₂— groups |
| 5.3-6.12 | H in position 2 of the 2-propenyl group |
| 6.3-7 | H in position 1 of the 3-terbutoxy, 3-oxo-1-propenyl group |
| 5.65-5.8 | H in position 2 of the 3-tertbutoxy, 3-oxo-1-propenyl group |
| 7.06 | aromatic H's |

EXAMPLE 5

4-(2-propenyl)-1-indanyl [1R-[1-alpha,3-alpha(E)]]-3-[3-(1,1-dimethylethoxy)-2-fluoro-3-oxo-1-propenyl]-2,2-dimethylcyclopropanecarboxylate $[alpha]_D = +31° \pm 1°$ c=1% CHCl₃

EXAMPLE 6

4-(2-propenyl)-1-indanyl [1R-[1-alpha(R*),3-alpha(E)]]-3-(3-ethoxy-2-fluoro-3-oxo-1-propenyl)-2,2-dimethylcyclopropanecarboxylate $[alpha]_D = +98° \pm 2°$ c=1% CHCl₃
Alcohol: (see preparation 22).

EXAMPLE 7

4-(2-propenyl)-1-indanyl [1R-[1-alpha(R*),3-alpha(E)]]-3-[3-(1,1-dimethylethoxy)-2-fluoro-3-oxo-1-propenyl-2,2-dimethylcyclopropanecarboxylate $[alpha]_D +104.5° \pm 2°$ c=0.85% CHCl₃

EXAMPLE 8

4-(2-propenyl)-1-indanyl [1R-[1-alpha(S*),3-alpha(E)]]-3-[3-(3-ethoxy-2-fluoro-3-oxo-1-propenyl)-2,2-dimethylcyclopropanecarboxylate $[alpha]_D = -53° \pm 1.5°$ c=1% CHCl₃

EXAMPLE 9

4-(2-propenyl)-1-indanyl [1R-[1-alpha(S*),3-alpha(E)]]-3-[3-(1,1-dimethylethoxy)-2-fluoro-3-oxo-1-propenyl]-2,2-dimethylcyclopropanecarboxylate $[alpha]_D = -33° \pm 1.5°$ c=1% CHCl₃

EXAMPLE 10

[cis(±)-2-fluoro-4-(1-propenyl)-1-indanyl][1R-[1-alpha,3-alpha(Z)]]-3-[3-(1,1-dimethylethoxy)-3-oxo-1-propenyl]-2,2-dimethylcyclopropanecarboxylate $[alpha]_D = +62.5° \pm 1.5°$ c=1% CHCl₃
Alcohol used: (see preparation 3).

EXAMPLE 11

[cis(±)-2-fluoro-4-(2-propenyl)-1-indanyl][1R-[1-alpha,3-alpha(E)]]-3-[3-ethoxy-2-fluoro-3-oxo-1-propenyl]-2,2-dimethylcyclopropanecarboxylate $[alpha]_D = +37.5° \pm 1.5°$ c=1% CHCl₃

EXAMPLE 12

1-fluoro-4-(2-propenyl)-2-indanyl [1R-[1-alpha,2-beta[1R*,3R*(E)]]] and [1S-[1-alpha,2-beta-[1S*,3S*(E)]]-3-(3-ethoxy-2-fluoro-3-oxo-1-propenyl)-2,2-dimethylcyclopropanecarboxylate $[alpha]_D = +51°$ c=0.5% CHCl₃
Starting alcohol: (see preparation 2)

EXAMPLE 13

[(RS,cis)-2-chloro-4-(2-propenyl)-1-indanyl][1R-[1-alpha,3-alpha(E)]]-3-[3-ethoxy-2-fluoro-3-oxo-1-propenyl]-2,2-dimethylcyclopropanecarboxylate $[alpha]_D = +30.5° \pm 1°$ c=1% CHCl₃
Alcohol used: (see preparation 4).

EXAMPLE 14

[(RS,cis)-2-chloro-4-(2-propenyl)-1-indanyl [1R-[1-alpha,3-alpha(Z)]]-3-[3-(1,1-dimethylethoxy-3-oxo-1-propenyl]-2,2-dimethylcyclopropanecarboxylate $[alpha]_D = -53.5° \pm 1.5°$ c=1% CHCl₃

EXAMPLE 15

(RS,trans)-2-chloro-4-(2-propenyl)-1-indanyl][1R-[1-alpha,3-alpha(E)]]-3-{3-ethoxy-2-fluoro-2-oxo-1-propenyl]-2,2-dimethylcyclopropanecarboxylate $[alpha]_D = +29° \pm 1°$ c=1% CHCl₃

EXAMPLE 16

2-methyl-4-(2-propenyl)-1-indanyl [1-alpha,3-alpha(E)]]-3-[3-ethoxy-2-fluoro-3-oxo-1-propenyl]-2,2-dimethylcyclopropanecarboxylate $[alpha]_D = +26.5° \pm 2.5°$ c=0.6% CHCl₃
Alcohol used: (see preparation 5).

EXAMPLE 17

2-methyl-4-(2-propenyl)-1-indanyl [1R-[1-alpha,3-alpha(Z)]]-3-[3-(1,1-dimethylethoxy)-3-oxo-1-propenyl]-2,2-dimethylcyclopropanecarboxylate $[alpha]_D = +51.5° \pm 1.5°$ c=0.7%

EXAMPLE 18

5-(2-propenyl)-1-indanyl [1R-[1-alpha(RS*),3-alpha(E)]]-3-[3-ethoxy-2-fluoro-3-oxo-1-propenyl]-2,2-dimethylcyclopropanecarboxylate $[alpha]_D = +24° \pm 2°$ c=0.5% CHCl₃
Alcohol: (see preparation 6).

EXAMPLE 19

5-(2-propenyl)-1-indanyl [1R-[1-alpha(RS*),3-alpha(Z)]]-3-[3-(1,1-dimethylethoxy)-3-oxo-1-propenyl]-2,2-dimethylcyclopropanecarboxylate $[alpha]_D = +55.5° \pm 1.5°$ c=0.8% CHCl₃

EXAMPLE 20

6-(2-propenyl)-1-indanyl [1R-[1-alpha(RS*),3-alpha(E)]]-3-[3-(1,1-dimethylethoxy)-2-fluoro-3-oxo-1-propenyl]-2,2-dimethylcyclopropanecarboxylate $[alpha]_D = +37° \pm 2.5°$ c=0.45% CHCl$_3$
See preparation 7 for the alcohol used.

EXAMPLE 21

6-(2-propenyl)-1-indanyl [1R-[1-alpha(RS*),3-alpha(E)]]-3-(3-ethoxy-2-fluoro-3-oxo-1-propenyl)-2,2-dimethylcyclopropanecarboxylate $[alpha]_D = +20° \pm 2.5°$ c=0.45% CHCl$_3$

EXAMPLE 22

2-indanyl [1R-[1-alpha,3-alpha(Z)]]-3-[3-(1,1-dimethylethoxy)-3-oxo-1-propenyl]-2,2-dimethylcyclopropanecarboxylate $[alpha]_D = +43° \pm 1.5°$ c=1% CHCl$_3$
Alcohol: (see preparation 8).

EXAMPLE 23

2-indanyl [1R-[1-alpha,3-alpha(E)]]-3-(3-ethoxy-2-fluoro-3-oxo-1-propenyl)-2,2-dimethylcyclopropanecarboxylate $[alpha]_D = +18.5° \pm 2°$ c=0.49% CHCl$_3$

EXAMPLE 24

1-indanyl [1R-[1-alpha(RS*),3-alpha(E)]]-3-(3-ethoxy-2-fluoro-3-oxo-1-propenyl)-2,2-dimethylcyclopropanecarboxylate $[alpha]_D = +28° \pm 2°$
Alcohol used: see preparation 9.

EXAMPLE 25

1-indanyl [1R-[1-alpha(RS*),3-alpha(Z)]]-3-[3-(1,1-dimethylethoxy)-3-oxo-1-propenyl]-2,2-dimethylcyclopropanecarboxylate $[alpha]_D = +59.5° \pm 2.5°$ c=0.4% CHCl$_3$

EXAMPLE 26

4-bromo-1-indanyl [1R-[1-alpha(RS*),3-alpha(Z)]]-3-[3-(1,1-dimethylethoxy)-3-oxo-1-propenyl]-2,2-dimethylcyclopropanecarboxylate $[alpha]_D = +44.5° \pm 2°$ c=0.4% CHCl$_3$
Alcohol used: (see Agr. Bio. Chem. 1978, 42, 1365).

EXAMPLE 27

4-bromo-1-indanyl [1R-[1-alpha(RS*),3-alpha(E)]]-3-(3-ethoxy-2-fluoro-3-oxo-1-propenyl)-2,2-dimethylcyclopropanecarboxylate $[alpha]_D = +22° \pm 1°$ c=0.7% CHCl$_3$

EXAMPLE 28

4-bromo-2-indanyl [1R-[1-alpha(RS*),3-alpha(E)]]-3-(3-ethoxy-2-fluoro-3-oxo-1-propenyl)-2,2-dimethylcyclopropanecarboxylate $[alpha]_D = +10.5° \pm 1°$ c=1% CHCl$_3$
Alcohol: (see preparation 1, stage C).

EXAMPLE 29

4-bromo-2-indanyl [1R-[1-alpha(RS*),3-alpha(Z)]]-3-[3-(1,1-dimethylethoxy)-3-oxo-1-propenyl]-2,2-dimethylcyclopropanecarboxylate $[alpha]_D = +41.5° \pm 1.5°$ c=1% CHCl$_3$

EXAMPLE 30

4-bromo-1-indanyl [1R-[1-alpha(RS*),3-alpha(E)]]-3-[3-(1,1-dimethylethoxy)-2-fluoro-3-oxo-1-propenyl]-2,2-dimethylcyclopropanecarboxylate $[alpha]_D = +23° \pm 1°$ c=0.7% CHCl$_3$

EXAMPLE 31

4-cyano-1-indanyl [1R-[1-alpha(RS*),3-alpha(Z)]]-3-[3-(1,1-dimethylethoxy)-3-oxo-1-propenyl]-2,2-dimethylcyclopropanecarboxylate $[alpha]_D = +58.5° \pm 2°$ c=0.75% CHCl$_3$
Alcohol: (see preparation 10. Agr. Biol. Chem. (1978), 42, 1365.

EXAMPLE 32

4-cyano-1-indanyl [1R-[1-alpha(RS*),3-alpha(E)]]-3-(3-ethoxy-2-fluoro-3-oxo-1-propenyl)-2,2-dimethylcyclopropanecarboxylate $[alpha]_D = +25.5° \pm 2°$ c=0.5% CHCl$_3$

EXAMPLE 33

4-cyano-2-indanyl [1R-[[1-alpha,3-alpha(E)]]]-3-(3-ethoxy-2-fluoro-3-oxo-1-propenyl)-2,2-dimethylcyclopropanecarboxylate $[alpha]_D = +3° \pm 2°$ c=0.3% CHCl$_3$
Alcohol: (see preparation 11).

EXAMPLE 34

4-cyano-2-indanyl [1R-[1-alpha,3-alpha(Z)]]-3-[3-(1,1-dimethylethoxy)-3-oxo-1-propenyl]-2,2-dimethylcyclopropanecarboxylate $[alpha]_D = +41° \pm 3°$ c=0.4% CHCl$_3$

EXAMPLE 35

4-cyano-1-indanyl [1R-[1-alpha(RS*),3-alpha(E)]]-3-(3-(dimethylethoxy)-2-fluoro-3-oxo-1-propenyl)-2,2-dimethylcyclopropanecarboxylate $[alpha]_D = +33° \pm 2.5°$ c=0.5% CHCl$_3$

EXAMPLE 36

4-cyano-1-indanyl [1R-[1-alpha(S*),3-alpha(E)]]-3-[3-(1,1-dimethylethoxy)-2-fluoro-3-oxo-1-propenyl]-2,2-dimethylcyclopropanecarboxylate $[alpha]_D = -51° \pm 1.5°$ c=0.75% CHCl$_3$
Alcohol (S): see preparation 13 (Stage C).

EXAMPLE 37

4-cyano-1-indanyl [1R-[1-alpha(S*),3-alpha(E)]]-3-(3-ethoxy-2-fluoro-3-oxo-1-propenyl)-2,2-dimethylcyclopropanecarboxylate $[alpha]_D = -77° \pm 2.5°$ c=0.5%

EXAMPLE 38

4-cyano-1-indanyl
[1R-[1-alpha(R*),3-alpha(E)]]-3-(3-ethoxy-2-fluoro-3-oxo-1-propenyl)-2,2-dimethylcyclopropanecarboxylate

[alpha]$_D$= +138°±2.5° c=0.8% CHCl$_3$
Alcohol (R): see preparation 13 (Stage B).

EXAMPLE 39

4-cyano-1-indanyl
[1R-[1-alpha(R*),3-alpha(E)]]-3-[3-(1,1-dimethylethoxy)-2-fluoro-3-oxo-1-propenyl]-2,2-dimethylcyclopropanecarboxylate

[alpha]$_D$= +135°±2.5° c=0.7% CHCl$_3$

EXAMPLE 40

5-cyano-1-indanyl
[1R-[1-alpha(RS*),3-alpha(E)]]-3-(3-ethoxy-2-fluoro-3-oxo-1-propenyl)-2,2-dimethylcyclopropanecarboxylate

[alpha]$_D$= +40.5°±2.5° c=0.4% CHCl$_3$
Alcohol: see preparation 12.

EXAMPLE 41

5-cyano-1-indanyl
[1R-[1-alpha(RS*),3-alpha(Z)]]-3-[3-(1,1-dimethylethoxy)-3-oxo-1-propenyl]-2,2-dimethylcyclopropanecarboxylate

[alpha]$_D$=61.5°±1.5° c=1% CHCl$_3$

EXAMPLE 42

6-cyano-1-indanyl
[1R-[1-alpha(RS*),3-alpha(E)]]-3-(3-ethoxy-2-fluoro-3-oxo-1-propenyl)-2,2-dimethylcyclopropanecarboxylate

[alpha]$_D$= +29.5°±1.5° c=1% CHCl$_3$
Alcohol: see preparation 14.

EXAMPLE 43

6-cyano-1-indanyl
[1R-[1-alpha(RS*),3-alpha(E)]]-3-[3-(1,1-dimethylethoxy-2-fluoro-3-oxo-1-propenyl]-2,2-dimethylcyclopropanecarboxylate

[alpha]$_D$= +41°±1.5° c=1% CHCl$_3$

EXAMPLE 44

7-cyano-1-indanyl
[1R-[1-alpha(RS*),3-alpha(E)]]-3-[3-(1,1-dimethylethoxy)-2-fluoro-3-oxo-1-propenyl]-2,2-dimethylcyclopropanecarboxylate

[alpha]$_D$= +18°±1° c=1% CHCl$_3$
Alcohol: see preparation 15.

EXAMPLE 45

7-cyano-1-indanyl
[1R-[1-alpha(RS*),3-alpha(E)]]-3-(3-ethoxy-2-fluoro-3-oxo-1-propenyl)-2,2-dimethylcyclopropanecarboxylate

[alpha]$_D$= −5°±1° c=0.7% CHCl$_3$

EXAMPLE 46

4-cyanomethyl-1-indanyl
[1R-[1-alpha(RS*),3-alpha(E)]]-3-(3-ethoxy-2-fluoro-3-oxo-1-propenyl)-2,2-dimethylcyclopropanecarboxylate

[alpha]$_D$= +23.5°±1.5° c=0.6% CHCl$_3$
See preparation 16 (alcohol RS).

EXAMPLE 47

4-cyanomethyl-1-indanyl
[1R-[1-alpha(RS*),3-alpha(Z)]]-3-[3-(1,1-dimethylethoxy)-3-oxo-1-propenyl]-2,2-dimethylcyclopropanecarboxylate

[alpha]$_D$= +54.5°±1° c=1% CHCl$_3$

EXAMPLE 48

4-(1-cyano-2-ethoxy-2-oxo-2-ethyl)-1-indanyl
[1R-[1-alpha(RS*),3-alpha(E)]]-(3-ethoxy-2-fluoro-3-oxo-1-propenyl)-2,2-dimethylcyclopropanecarboxylate NMR Spectrum CDCl$_3$ 60 MHz ppm 1.16–1.46: H of the twinned methyl groups and in position 2 ethoxy sub-groups
4.07–4.45: H in position 1 of an ethoxy sub-group
1.8–1.94–2.08 to 3.31: H in position 1 and 3 of the cyclopropane and in position 2 and 3 of the 1-indanyl group
7.35: aromatics
4.74: H in alpha position of the CN
6.08–6.16–6.25: H in position 1 of an ethoxy sub-group
6.16–6.33–6.5–6.6: ethylene H's
Alcohol RS: see preparation 17.

EXAMPLE 49

4-(1-cyano-2-ethoxy-2-oxo-ethyl)-1-indanyl
[1R-[1-alpha(RS*),3-alpha(Z)]]-3-[3-(1,1-dimethylethoxy)-3-oxo-1-propenyl]-2,2-dimethylcyclopropanecarboxylate NMR Spectrum CDCl$_3$ 60 MHz ppm 1.25–1.31: twinned CH$_3$
1.47: tBu
1.16–1.28–1.40: H in position 2 of the ethyl group
4.06–4.18–4.3–4.38: H in position 1 of the ethyl group
1.82–1.95: H$_1$ cis of the cyclopropyl
2.13–3.38: H$_3$ of the cyclopropyl and the CH$_2$'s
4.74: H in alpha position of the CN
5.68–5.87–6.34–6.53–6.50–6.7: ethylene H's
7.35: aromatics
See preparation 17 (alcohol RS)

EXAMPLE 50

4-propyl-1-indanyl
[1R-[1-alpha(RS*),3-alpha(E)]]-3-(3-ethoxy-2-fluoro-3-oxo-1-propenyl)-2,2-dimethylcyclopropanecarboxylate

[alpha]$_D$= +18°±2° c=0.6% CHCl$_3$
Alcohol used: see preparation 18.

EXAMPLE 51

4-propyl-1-indanyl
[1R-[1-alpha(RS*),3-alpha(E)]]-3-(3-dimethylethoxy-2-fluoro-3-oxo-1-propenyl)-2,2-dimethylcyclopropanecarboxylate

[alpha]$_D$= +35.5° c=1% CHCl$_3$

EXAMPLE 52

4-(2-methyl-2-propenyl)-1-indanyl
[1R-[1-alpha,3-alpha(E)]]-3-(3-ethoxy-2-fluoro-3-oxo-1-propenyl)-2,2-dimethylcyclopropanecarboxylate

[alpha]$_D$= +20°±1° c=1% CHCl$_3$
Alcohol used: see preparation 19.

EXAMPLE 53

4-(2-methyl-2-propenyl)-1-indanyl [1R-[1-alpha,3-alpha(Z)]]-2,2-dimethyl-3-[3-(1,1-dimethylethoxy)-3-oxo-1-propenyl]-cyclopropanecarboxylate

[alpha]$_D$= +48.5°±1.5° c=1% CHCl$_3$

EXAMPLE 54

4-(2-propynyl)-1-indanyl [1R-[1-alpha(RS*),3-alpha(E)]]-3-(3-ethoxy-2-fluoro-3-oxo-1-propenyl)-2,2-dimethylcyclopropanecarboxylate

[alpha]$_D$= +22.5°±2° c=0.5% CHCl$_3$

Alcohol used: see preparation 20. Agr. Biol. Chem. 1978, 42, 1365.

EXAMPLE 55

4-(2-propynyl)-1-indanyl [1R-[1-alpha(RS*),3-alpha(Z)]]-3-[3-(1,1-dimethylethoxy)-3-oxo-1-propenyl]-2,2-dimethylcyclopropanecarboxylate

[alpha]$_D$= +51°±2.5° c=0.5% CHCl$_3$

EXAMPLE 56

4-(2-propynyl)-2-indanyl [1R-[1-alpha(RS*),3-alpha(E)]]-3-(3-ethoxy-2-fluoro-3-oxo-1-propenyl)-2,2-dimethylcyclopropanecarboxylate NMR Spectrum CDCl$_3$ 60 MHz ppm 1.25: twinned Me
1.21-1.33-1.45: H of the CH$_3$ of the ethoxy group
4.1-4.45: H of the CH$_2$ of the ethoxy group
1.75-1.9: H$_1$ of the cyclopropane (cis position)
2.63-2.95: H$_3$
3.0-3.25: H in position 1 and 3 of the 2-indanyl
5.35-5.68: H in position 2 of the 2-indanyl
2.1-2.13-2.2: H in position 3 of the 2-propynyl group
3.45-3.5: H in position 1 of the 2-propynyl group
6.1-6.28-6.46-6.63: ethylene H's
7.06-7.25: aromatics Alcohol used: see preparation 20.

EXAMPLE 57

4-(2-propynyl)-2-indanyl [1R-[1-alpha(RS*),3-alpha(Z)]]-3-[3-(1,1-dimethylethoxy)-3-oxo-1-propenyl]-2,2-dimethylcyclopropanecarboxylate NMR Spectrum CDCl$_3$ 60 MHz ppm 1.22-1.3: twinned Me
1.47: tBu
1.18-1.92: H$_1$ cis and the CH$_2$'s
2.73-3.34: H$_3$
5.33-5.68: CH$_2$-CH-CH$_2$ 2.08-2.13-2.18: CH$_2$—C CH
6.33-6.74

7.1-7.29: aromatics

EXAMPLE 58

4-(2-propynyl)-1-indanyl [1R-[1-alpha(RS*),3-alpha(E)]]-3-[3-(1,1-dimethylethoxy)-2-fluoro-3-oxo-1-propenyl]-2,2-dimethylcyclopropanecarboxylate

[alpha]$_D$= +30°±2.5° c=0.4% CHCl$_3$

EXAMPLE 59

4-ethenyl-1-indanyl [1R-[1-alpha(RS*),3-alpha(Z)]]-3-[3-(1,1-dimethylethoxy)-3-oxo-1-propenyl]-2,2-dimethylcyclopropanecarboxylate

[alpha]$_D$= +51.5°±2.5° c=0.5% CHCl$_3$

EXAMPLE 60

4-ethenyl-1-indanyl [1R-[1-alpha(RS*),3-alpha(E)]]-3-(3-ethoxy-2-fluoro-3-oxo-1-propenyl)-2,2-dimethylcyclopropanecarboxylate

[alpha]$_D$= +17.5°±2.5° c=0.5% CHCl$_3$.

The starting alcohol is prepared according to the process described in Agr. Biol. Chem. 1978, 42, 1365.

EXAMPLE 61

4-ethynyl-1-indanyl [1R-[1-alpha(RS*),3-alpha(E)]]-2,2-dimethyl-3-(2-fluoro-3-ethoxy-3-oxo-1-propenyl)-cyclopropanecarboxylate

[alpha]$_D$= +17.5°±2° c=0.5% CHCl$_3$

EXAMPLE 62

4-ethynyl-1-indanyl [1R-[1-alpha(RS*),3-alpha(Z)]]-3-[3-(1,1-dimethylethoxy)-3-oxo-1-propenyl]-2,2-dimethylcyclopropanecarboxylate

[alpha]$_D$= +50°±2.5° c=0.5% CHCl$_3$

The corresponding starting alcohols are prepared according to the process described in Agr. Biol. Chem. 1978, 42, 1365.

EXAMPLE 63

4-(2-chloro-2-propenyl)-1-indanyl [1R-[1-alpha,3-alpha(E)]]-3-[3(1,1-dimethylethoxy)-2-fluoro-3-oxo-1-propenyl]-2,2-dimethylcyclopropanecarboxylate

[alpha]$_D$= +27°±3° c=0.4% CHCl$_3$

Alcohol used: see preparation 21.

EXAMPLE 64

4-(2-chloro-2-propenyl)-1-indanyl [1R-[1-alpha,3-alpha(E)]]-3-[3-ethoxy-2-fluoro-3-oxo-1-propenyl]-2,2-dimethylcyclopropanecarboxylate

[alpha]$_D$= +20°±1.5° c=0.8% CHCl$_3$

EXAMPLE 65

4-tributylstannyl-1-indanyl [1R-[1-alpha,3-alpha(Z)]]-3-[3-(1,1-dimethylethoxy)-3-oxo-1-propenyl]-2,2-dimethylcyclopropanecarboxylate

[alpha]$_D$= +33°±1.5° c=1% CHCl$_3$

EXAMPLE 66

3,3-dimethyl-1-indanyl
[1R-[1-alpha(RS*),3-alpha(E)]]-3-(3ethoxy-2-fluoro-3-oxo-1-propenyl)-2,2-dimethylcyclopropanecarboxylate

[alpha]$_D$= +31° c=0.3% CHCl$_3$

EXAMPLE 67

3,3-dimethyl-1-indanyl
[1R-[1-alpha(RS*),3-alpha(Z)]]-3-[3-(1,1-dimethylethoxy)-3-oxo-1-propenyl]-2,2-dimethylcyclopropanecarboxylate

[alpha]$_D$= +64° c=0.4% CHCl$_3$

PREPARATION 1

(RS) 4-(2-propenyl)-2-indanol

Stage A: 4-bromo-3H-indene 30 g of 4-bromo-1-indanol is dissolved in 720 ml of toluene, 27 g of paratoluene sulphonic acid is added, then 0.93 g of 4-tertbutylcatechol is added. The mixture is taken to reflux for one hour. After cooling to 20° C., the organic phase is washed with 25 ml of N sodium hydroxide, dried and concentrated to dryness, and the residue is chromatographed on silica, eluting with a hexane-difluoro dichloro ethane mixture (95-5), and 24.6 g of expected product is isolated.

| IR Spectrum CHCl$_3$ | |
|---|---|
| c=c | 1602 cm$^{-1}$ |
|  | 1576 cm$^{-1}$ |

Aromatic 1544 cm$^{-1}$

Stage B: 4-bromo-2-indanol 260 ml of tetrahydrofuran borohydride complex (0.8M in tetrahydrofuran) is cooled to −5°, −10° C., and drop by drop 22.8 ml of 2,3-dimethyl-2-butene in 115 cm$^3$ of tetrahydrofuran is added and the whole is left for one hour at 0°/+5° C. After cooling to −5° C. a solution of 17 g of 4-bromo-indene in 170 ml of tetrahydrofuran is added drop by drop, agitation is maintained for ¼ hour at 0° C., and the temperature is allowed to rise slowly (over 2 hours) to +15° C. After cooling to 0° C., 23 ml of water is introduced, without exceeding +5° C., with further agitation for 5 minutes, and then 85 ml of 2N sodium hydroxide is added without exceeding +15° C., with agitation for 5 minutes; then, maintaining the temperature between 40° C. and 45° C., 85 ml of hydrogen peroxide (at 30%) is added. After further agitation for 7 hours at ambient temperature, the reaction mixture is poured over 500 ml of water and 300 ml of isopropyl ether; the mixture is decanted and extracted with isopropyl ether. The organic phases are reunited, dried and concentrated to dryness. The residue is chromatographed on silica, eluting with a hexane-ethyl acetate mixture (75-25), and 18.05 g of the following mixture is obtained: 74% of expected product and 23% of hydroxylated product in position 1. The mixture is taken to reflux for 5 minutes in 90 ml of anhydrous toluene containing 0.8 g of hydrated paratoluene sulphonic acid (APTS, 1H$_2$O). After concentrating to dryness, the residue is chromatographed on silica, eluting with a hexane-ethyl acetate mixture (7-3), and 11.6 g of expected product is obtained, M.p.=80° C.

Stage C: [4-bromo-(2-indanyl)-oxy]-trimethyl silane 5.2 ml of anhydrous triethylamine is added drop by drop to 5.3 g of product obtained in Stage B in 50 ml of methylene chloride. After cooling to 0°, +5° C., 3.5 ml of trimethylsilyl chloride in 15 ml of methylene chloride is introduced drop by drop, with agitation for 5 minutes at 0° C. and for 15 minutes at ambient temperature. The reaction mixture is poured into 200 ml of a water and ice mixture and 100 ml of isopropyl ether. After decanting, the organic phase is washed with water to obtain a pH of 7.5-8, and the aqueous phases with water are extracted by isopropyl ether. The organic phases are reunited, dried, concentrated to dryness and 6.81 g of expected product is obtained.

| IR Spectrum CHCl$_3$ | |
|---|---|
| Aromatic | 1602 cm$^{-1}$ |
|  | 1569 cm$^{-1}$ |
| —O—Si | 1252 cm$^{-1}$ |
|  | 843 cm$^{-1}$ |

Stage D: (RS) 4-(2-propenyl)-2-indanol 5.50 g of product obtained above is agitated in 30 ml of anhydrous tetrahydrofuran, cooled to −65° C. and 15.7 ml of a 1.6M butyllithium solution in hexane is introduced over half an hour, followed by agitation for one and a half hours at −65° C. 2.21 g of dry cuprous chloride is added in one lot and the suspension obtained is left for half an hour at −65° C. The latter is added in small amounts and under inert atmosphere to a solution, cooled to −70° C., of 4.20 ml of bromoallyl in 21 ml of tetrahydrofuran and the mixture is left for one hour at −70° C., −65° C. The reaction mixture is poured into 200 ml of 2N hydrochloric acid containing ice and 100 ml of isopropyl ether, then agitated for one hour at ambient temperature. The insoluble part is filtered off, decanted, the organic phase is washed with water, and the aqueous phases are extracted with isopropyl ether. The reunited organic phases are dried, concentrated to dryness, and the residue is chromatographed on silica, eluting with a hexane-ethyl acetate mixture (8-2). 0.89 g of expected product is obtained, and 1.04 g of expected impure product is obtained, which is chromatographed again in the same conditions, and 0.75 g of expected product is recovered.

| IR Spectrum CHCl$_3$: | | |
|---|---|---|
| Aromatics |  | 1596 cm$^{-1}$ |
| —OH | to | 3615 cm$^{-1}$ |
|  |  | 1638 cm$^{-1}$ |
| —CH=CH$_2$ |  | 995 cm$^{-1}$ |
|  |  | 917 cm$^{-1}$ |

PREPARATION 2

[(1-alpha(RS),2-beta(RS)]-1-fluoro-4-(2-propenyl)-2-indanol

Stage A: 4-bromo-1,2-epoxyindene 250 ml of pH 8 phosphate buffer, 150 ml of methylene chloride, 200 mg of tetrabutylammonium hydrogenosulphate and 10 g of 4-bromo-3H-indene are mixed together. At 0° C. 10 g of metachloroperbenzoic acid is added in several lots, then the temperature of the mixture is allowed to rise to the ambient over 4 hours, 10 g of metachloroperbenzoic acid is added at 0° C. and the temperature is allowed to rise to 20° C. over 2 hours. 3 g of metachloroperbenzoic acid is added and the mixture is left for 16 hours at ambient temperature, then decanted and extracted with methylene chloride; the extracts are washed with water, with a thiosulphate solution and with water, dried and evaporated to dryness. The residue is chromatographed on silica, eluting with a mixture of hexane and isopropyl ether (9-1) with 3% of triethylamine, and 4.11 g of expected product is isolated.

Stage B:
[1-alpha(RS),2-beta(RS)]-4-bromo-1-fluoro-2-indanol 5 ml of dimethylformamide hydrofluoric acid complex is cooled to −30° C., 0.6 g of epoxide obtained above in 3 ml of dimethylformamide is added drop by drop and the whole is left for one hour at −30° C. The reaction mixture is poured over 100 g of ice and 15 ml of concentrated ammonia, and extracted with ether; the extracts are washed with a saturated solution of monopotassium phosphate until neutral, then dried and concentrated to dryness. The residue is chromatographed on silica, eluting with a hexane-ethyl acetate mixture (8-2), and 0.31 g of expected product is isolated, M.p.=71° C.

Stage C:
[1-alpha(RS),2-beta(RS)]-1-fluoro-4-(2-propenyl)-2-indanol 2.3 g of product obtained above, 20 ml of dimethylformamide, 400 mg of tetrakis(triphenyl phosphine) palladium and 4 ml of (2-propenyl)-tributyl stannane are taken to reflux at 120° C. for 3 hours. The mixture is poured over 100 ml of a 1M solution of potassium fluoride in water. After filtering, the insoluble part is rinsed with isopropyl ether and the filtrate is extracted with isopropyl ether; the organic phases are dried and concentrated to dryness. The residue is chromatographed on silica, eluting with a hexane-ethyl acetate mixture (8-2) and 0.5 g of expected product is isolated with ether, washed with a saturated aqueous solution of monopotassium phosphate, then with water, dried and concentrated to dryness.

PREPARATION 3 cis (±) 2-fluoro-4-(2-propenyl)-1-indanol

Stage A: 4-(2-propenyl)-1-indanone 15 g of 4-bromo-1-indanone, 24 ml of tributyl allyl stannane, 150 ml of dimethylformamide, 0.82 g of tetrakis triphenyl phosphine palladium and 7.89 g of triethylamine are taken to 120° C. for one hour. After cooling to 20° C., the reaction mixture is poured over 300 ml of an aqueous solution of potassium fluoride, agitated, and filtered on celite; the filtrate is extracted with isopropyl ether. The insoluble part is taken up with ethyl acetate and filtered on celite. The reunited organic phases are washed with water saturated with sodium chloride, dried and brought to dryness under reduced pressure. The residue is chromatographed on silica with hexane-ethyl acetate (9-1) and 11.84 g of expected product is recovered.

| IR Spectrum in CHCl₃: | |
|---|---|
| C=O | 1703 cm⁻¹ |
| —CH=CH₂ | 1640 cm⁻¹ |
| | 922 cm⁻¹ |
| | 996 cm⁻¹ |
| Aromatic | 1602 cm⁻¹ |
| | 1592 cm⁻¹ |
| | 1483 cm⁻¹ |

Stage B: 3-trimethylsilyloxy-7-(2-propenyl)-indene 1.24 ml of diisopropylamine and 6 ml of tetrahydrofuran are cooled to −40° C., then 4.7 ml of butyllithium is added drop by drop. The temperature is allowed to rise to −20° C., agitation is carried out for ¼ hour, then 1 g of 4-(2-propenyl)-1-indanone in 10 ml of tetrahydrofuran is introduced at −70° C. After agitation for one hour at −60° C., 1.15 ml of trimethylsilyl chloride in 6 ml of tetrahydrofuran is added, with agitation for one hour at −60° C. The mixture is poured over 100 ml of water and ice and 100 ml of ether. After decanting, the aqueous phase is extracted with ether, the organic phases are reunited, dried and concentrated to dryness without heating, and 1.51 g of expected product is isolated.

Stage C: 2-fluoro-4-(2-propenyl)-1-indanone 4.58 g of product obtained above is agitated for 5 minutes in 50 ml of methylene chloride; 6.03 g of N-fluoropyridine trifluoromethyl sulphonate is introduced in one lot and the whole is taken to reflux for 5 hours. The reaction mixture is poured over 250 ml of water and ice and 250 ml of methylene chloride. After decanting and washing with water, the aqueous phases are extracted with methylene chloride, dried and concentrated to dryness. The residue is chromatographed on silica, eluting with a hexane-isopropyl ether mixture (85-15) and 2.69 g of expected product is obtained.

| IR Spectrum CHCl₃: | |
|---|---|
| C=O | 1729 cm⁻¹ |
| —CH₂=CH₂ | 1640 cm⁻¹ |
| | 921 cm⁻¹ |
| Aromatic | 1603 cm⁻¹ |
| | 1592 cm⁻¹ |
| | 1483 cm⁻¹ |

Stage D: cis (±) 2-fluoro-4-(2-propenyl)-1-indanol and its trans (±) isomer 2.62 g of product obtained above is agitated for 5 minutes in 50 ml of 90° ethanol, cooled to 0° C. and 0.37 g of sodium borohydride is introduced in several lots, then the whole is agitated for one hour at 0° C. After concentrating to dryness under reduced pressure, the residue is taken up in 100 ml of water and 100 ml of methylene chloride. After decanting, the aqueous phase is extracted with methylene chloride, dried and concentrated to dryness under reduced pressure. The residue is chromatographed on silica in a hexane-isopropyl ether mixture (7-3) and 0.21 g of crude trans isomer is isolated, which is chromatographed again so as to obtain 0.14 g of trans isomer and 1.72 g of expected product (cis isomer).

| IR Spectrum CHCl₃ (cis isomer) | |
|---|---|
| —OH | 3590 cm⁻¹ |
| CH₂=CH | 3080 cm⁻¹ |
| | 1639 cm⁻¹ |
| | 919 cm⁻¹ |

PREPARATION 4

[1-alpha(R),2-alpha(S)]+[1-alpha(S),2-alpha(R)]-2-chloro-4-(2-propenyl)-1-indanol Stage A: 2-chloro-4-(2-propenyl)-1-indanone 8 g of 3-trimethylsilyloxy-7-(2-propenyl)-indene in 25 ml of 1,2-dichloroethane is cooled to 0° C.; 31 g of N-chlorosuccinimide in 80 ml of dichloroethane is introduced over 25 minutes, with agitation for 30 minutes at 0° C.; 0.6 g of N-chlorosuccinimide in 15 ml of dichloroethane and a few mg of paratoluene sulphonic acid are added. After 30 minutes of agitation at 0° C., the reaction mixture is poured over an iced aqueous solution saturated with monopotassium phosphate, with agitation for 16 hours at 20° C. After decanting and extracting with methylene chloride, the extracts are dried, and concentrated to dryness under reduced pressure. The residue is chromatographed on silica, eluting with a hexane-isopropyl ether mixture (7-3). The fractions recovered are concentrated and chromatographed again on silica, eluting with a hexane-isopropyl ether mixture (3-1) and 2.75 g of expected product is isolated.

| NMR Spectrum 60 MHz (CDCl₃) ppm: |
|---|
| 4.40 to 4.75 (m, ABX system) CH∼Cl |
| 3.37 to 4.47 (m, ABX system)-CHCl—C H₂ — |
| 3.98 (d, 2H)-C H₂ —CH=CH₂ |
| 5.62 to 6.37 (m) CH₂—C(H)=CH₂ |
| 4.8 to 5.37 CH₂—CH=C H₂ |
| 7.15 to 7.8 aromatic |

Stage B:
[1-alpha(R),2-alpha(S)]+[1-alpha(S),2-alpha(R)]-2-chloro-4-(2-propenyl)-1-indanol 2.69 g of product obtained above in 50 ml of ethanol is cooled to 0° C., 260 mg of sodium borohydride at 95% is added and agitation is carried out for 30 minutes at 0° C. The mixture is poured over an iced aqueous saturated solution of monopotassium phosphate. After extraction with ether, the extracts are dried and concentrated to dryness under reduced pressure. The residue is chromatographed on silica, eluting under pressure with a methylene chloride-hexane-isopropyl ether mixture (3-6-1) and 2.28 g of expected product is recovered, RS cis, M.p.=54° C. and 0.19 g of RS trans product, M.p.=64° C.

PREPARATION 5

(cis+trans) 2-methyl-4-(2-propenyl)-1-indanol

Stage A: 2-methyl-4-(2-propenyl)-1-indanone 1.88 g of sodium methylate in 15 ml of ethyl ether is cooled to 0° C., a solution composed of 2.8 ml of ethyl formiate and 3 g of 4-(2-propenyl)-indanone in 6 ml of ether is introduced over 15 minutes, 5 ml of ether is added, with agitation for 15 minutes, and the suspension is allowed to rise to 20° C. 70 ml of dimethylformamide is added, with agitation for 2 hours, 2.15 ml of methyl iodide and 2 ml of ether are introduced, followed by agitation for 2 hours. The resulting mixture is then poured over 100 ml of ice water and extracted with ethyl ether, the extracts are dried and the solvent is evaporated under reduced pressure. The residue is chromatographed on silica, eluting with a hexane-ethyl acetate mixture (95-5) and 1.62 g of expected product is obtained.

| IR Spectrum: | |
|---|---|
| c=O | 1707 cm⁻¹ |
| CH₂=CH— | 1639 cm⁻¹ |
| | 921 cm⁻¹ |
| | 990 cm⁻¹ |
| | 3085 cm⁻¹ |
| Aromatic | 1603 cm⁻¹ |
| | 1591 cm⁻¹ |
| | 1490 cm⁻¹ |
| CH₃= | 1374 cm⁻¹ |

Stage B: (cis+trans) 2-methyl-4-(2-propenyl)-1-indanol 1.6 g of product obtained at A in 30 ml of 90° ethanol is cooled to 0° C., 170 mg of sodium borohydride at 95% is introduced and the reaction mixture is allowed to rise to 20° C. After one hour of agitation, 170 mg of sodium borohydride is added, with agitation for 3 hours. The ethanol is evaporated under reduced pressure, the aqueous solution is diluted with 10 ml of water and extracted with methylene chloride. The organic phase is dried, the solvent is evaporated under reduced pressure and the residue is chromatographed on silica, then eluted with a hexane-ethyl acetate mixture. 1.52 g of expected product is obtained (mixture).

| IR Spectrum: | |
|---|---|
| —OH∼ | 3600 cm⁻¹ |
| CH₂=CH— | 1639 cm⁻¹ |
| | 918 cm⁻¹ |
| | 997 cm⁻¹ |
| Aromatic | 1600 cm⁻¹ |
| | 1476 cm⁻¹ |

PREPARATION 6

(RS) 5-(2-propenyl)-1-indanol

Stage A: Diethyl 2-(3-bromobenzyl) malonate 11.52 g of sodium hydride at 50% in oil is added in fractions to 120 ml of dimethylformamide and 285 ml of toluene; the mixture is agitated for 10 minutes and cooled to 0° C. 36 ml of ethyl malonate in 36 ml of toluene is introduced over 15 minutes, followed by agitation for one hour at 0°+5° C. The reaction mixture obtained above is added drop by drop over 2 hours 15 minutes at 20° C. to 30 g of 3-bromobenzyl bromide and 150 ml of toluene. After agitation for 4 hours, the medium is poured into 500 ml of water. Extraction is carried out with isopropyl ether; the organic phase is washed with 240 ml of N hydrochloric acid, until pH 4 is obtained, then with water until pH 7 is obtained. After drying and filtering, the filtrate is brought to dryness under reduced pressure. The residue is chromatographed on silica, eluting with a hexane-ethyl acetate mixture (9-1) and 24.07 g of expected product and a dibromobenzylated product are obtained.

| IR Spectrum CHCl₃ | |
|---|---|
| C=O | 1745 cm⁻¹ |
| | 1730 cm⁻¹ |
| Aromatic | 1599 cm⁻¹ |
| | 1570 cm⁻¹ |
| | 1479 cm⁻¹ |

Stage B: 2-(3-bromobenzyl) malonic acid 25 g of product obtained above and 25 g of potassium hydroxide in 25 ml of water are taken to reflux for 5 hours 30 minutes. The precipitate is taken up in 300 ml of water and washed with isopropyl ether; 60 ml of hydrochloric acid concentrated to pH 1 is added to the aqueous phase while being cooled. Extraction is carried out with isopropyl ether, the extracts are washed with water, dried and brought to dryness under reduced pressure. The residue is taken up in 200 ml of hexane, followed by agitation for one hour, filtering and drying, and 18.85 g of expected product is recovered. M.p.=117° C.

Stage C: 3-(3-bromophenyl)-propionic acid 18.85 g of product obtained above in 75 ml of water is taken to reflux for 18 hours. Extraction is carried out with isopropyl ether, the extracts are dried, brought to dryness under reduced pressure, and 15.75 g of expected product is obtained. M.p.=74° C.

Stage D: 5-bromo-1-indanone and 7-bromo-1-indanone 15.7 g of product obtained in Stage C and 80 ml of thionyl chloride are taken to reflux for one hour 30 minutes and the excess thionyl chloride is distilled off under reduced pressure. 300 ml of methylene chloride and 11.5 g of aluminium chloride are added, then the whole is taken to reflux for 3 hours. After diluting with 200 ml of N hydrochloric acid and ice, extraction is carried out with methylene chloride; the organic phase is washed with water until pH 7 is obtained, dried and brought to dryness under reduced pressure. The residue is chromatographed on silica, eluting with methylene chloride, and 2.09 g of 7-bromo-1-indanone, 1.48 g of a mixture of the indanones and 9.21 g of 5-bromo-1-indanone are recovered. The mixture is chromatographed on silica, eluting with a hexane-ethyl acetate mixture (8-2), and 0.75 g of 5-bromo-1-indanone and 0.66 g of 7-bromo-1-indanone are separated out. 5-bromo-1-indanone M.p.=130° C. 7-bromo-1-indanone M.p.=114° C.

Stage E: 5-bromo-1-indanol (racemic)

1.5 g of product obtained in Stage D is dissolved in 15 ml of anhydrous ethanol and 5 ml of tetrahydrofuran; 0.19 g of sodium hydroboride at 95% is added, and the mixture is agitated for one hour 30 minutes at 20° C., then brought to dryness under reduced pressure. The residue is taken up in 100 ml of water containing sodium chloride and 100 ml of methylene chloride. After decanting, extraction is water saturated with sodium chloride, dried and brought to dryness under reduced pressure. 1.52 g of expected product is obtained, M.p.=73° C.

Stage F: 5-(2-propenyl)-1-indanol (racemic)

4.67 g of product obtained above, 46 ml of dimethylformamide, 7.98 g of tributylallylstannane and 1.39 g of tetrakis triphenyl phosphine palladium are taken to 140° C. for 45 minutes. After cooling, the reaction mixture is poured into 200 ml of water containing potassium fluoride, agitated for 15 minutes, filtered and rinsed with ethyl acetate. The filtrate is extracted with ethyl acetate, washed with water, dried and brought to dryness under reduced pressure. The residue is chromatographed on silica in a hexane-ethyl acetate mixture (7-3) and 2.92 g of expected product is obtained, which is taken up in 30 ml of pentane, agitated for one hour, filtered, dried at 45° C. and 2.55 g of product is recovered, M.p.=54° C.

PREPARATION 7

6-(2-propenyl)-1-indanol

The operation is carried out as in preparation 6 starting with 4-bromobenzyl bromide and the expected product is obtained.

| IR Spectrum CHCl₃: | |
|---|---|
| OH | 3597 cm⁻¹ |
| CH₂=CH | 3080 cm⁻¹ |
| | 1639 cm⁻¹ |
| | 918 cm⁻¹ |
| | 996 cm⁻¹ |

PREPARATION 8

2-indanol 3.0 g of 4-bromo-2-indanol (RS), 60 ml of tetrahydrofuran, 1.6 g of anhydrous sodium carbonate and 0.28 g of palladium at 10% on active charcoal are agitated for 5 minutes. A solution of 1.36 g of sodium hypophosphite in 8 ml of water is introduced over 10 minutes and the whole is taken to 50° C. for 2 hours. 1.60 g of sodium carbonate is added, then at 50° C. 1.36 g of sodium hypophosphite in 8 ml of water is added drop by drop. The mixture is heated for 3 hours, and after cooling it is filtered. The filtrate is rinsed with isopropyl ether, with methanol, and concentrated to dryness under reduced pressure. The residue is taken up in 150 ml of isopropyl ether and 150 ml of water. After decanting, extraction is carried out with isopropyl ether; the extracts are dried and brought to dryness under reduced pressure. The residue is chromatographed on silica in a hexane-ethyl acetate mixture (7-3) and 1.6 g is obtained, M.p.=69° C.

PREPARATION 9

1-indanol (racemic)

Stage A: 1-indanone

The operation is carried out as in preparation 8, starting with 2.8 g of 4-bromo-1-indanone and 1.28 g of expected product is obtained.

| IR Spectrum in CHCl₃ | |
|---|---|
| C=O | 1708 cm⁻¹ |
| Aromatic | 1610 (max) |
| | 1600 (ep), 1592 (ep) |

Stage B: 1-indanol (racemic)

1.28 g of 1-indanone in 13 ml of anhydrous ethanol is cooled to +5° C. 0.23 g of sodium borohydride at 95% is added in small fractions, with agitation at +10° C. for one hour. 0.23 g of sodium borohydride at 95% is again added at +5° C., with agitation at 20° C. for one hour 30 minutes. The reaction mixture is poured into 60 ml of water containing sodium chloride and is extracted with isopropyl ether; the extracts are dried and brought to dryness under reduced pressure and the residue is chromatographed on silica in a hexane-ethyl acetate mixture (6-4). 1.15 g of expected product is isolated.

| IR Spectrum CHCl$_3$: | |
|---|---|
| OH= | 3600 cm$^{-1}$ |
| | 1478 cm$^{-1}$ |

PREPARATION 10

1-hydroxy-4-indanecarbonitrile (racemic)

1.46 g of 4-cyano-1-indanone in 131 ml of tetrahydrofuran is cooled to +5° C., 1 g of potassium borohydride is added in small fractions, with agitation for one hour 15 minutes, followed by pouring over 200 ml of water containing sodium chloride, and extraction with isopropyl ether. The organic phase is dried, brought to dryness under reduced pressure and the residue is chromatographed on silica in a hexane-ethyl acetate mixture (6-4). 1.40 g of expected product is obtained, M.p.=98° C.

PREPARATION 11

(RS) 2-hydroxy-4-indanecarbonitrile

Stage A: 7-indanecarbonitrile 5.9 g of 1-hydroxy-4-indanecarbonitrile in 60 ml of 1,2,-dichloroethane and 210 mg of paratoluene sulphonic acid (APTS, 1H$_2$O) are taken to reflux for 2 hours. After cooling to ambient temperature and concentrating to dryness at 40° C. under reduced pressure, the residue is chromatographed on silica in a hexane-isopropyl ether mixture (9-1), and 2.46 g of expected product is isolated.

| IR Spectrum: | |
|---|---|
| C≡N | 2283 cm$^{-1}$ |
| C≡C | 1599 cm$^{-1}$ |
| Aromatic | 1468 cm$^{-1}$ |

Stage B: (RS) 2-hydroxy-4-indanecarbonitrile 42 ml of a 1M solution of boran-tetrahydrofuran complex is cooled to 0° C., 3.7 ml of 2,3-dimethyl-2-butene in 20 ml of tetrahydrofuran is added and agitation is carried out for one hour 15 minutes at 0° C. 1.98 g of product obtained in Stage A in 20 ml of tetrahydrofuran is introduced at 0° C. over 40 minutes, with agitation for ¼ hour at 0° C., and the temperature is allowed to rise to +14° C. over 3 hours. After cooling to 0° C., 5 ml of water is added drop by drop with agitation for 5 minutes, then 18 ml of 2N sodium hydroxide is introduced at +2° C., and the temperature is allowed to rise to +15° C. 18 ml of hydrogen peroxide at 30% is added slowly and the mixture is left under agitation for 17 hours. The reaction mixture is poured into 100 ml of water and 100 ml of isopropyl ether and decanted; the aqueous phase is extracted with isopropyl ether. The reunited organic phases are washed with water, dried and concentrated to dryness under reduced pressure. The residue is chromatographed on silica in a hexane-ethyl acetate mixture (6-4), and 0.15 g of expected product is obtained, and 1.15 g of impure product is obtained which is chromatographed again on silica in a hexane-ethyl acetate mixture (65-35) so as to obtain 0.74 g of expected product, M.p.=60° C.

PREPARATION 12

(RS) 1-hydroxy-5-indanecarbonitrile

The operation is carried out as in preparation 10, starting with 5-cyano-1-indanone (1.93 g), the extracted residue is taken up in 20 ml of hexane, with agitation for one hour. After filtering, the filtrate is dried at 45° C. under reduced pressure and 1.92 g is obtained, M.p.=94° C.

PREPARATION 13

1-hydroxy-4-indanecarbonitrile R(+) and 1-hydroxy-4-indanecarbonitrile S(−)

Stage A: (4-cyano-1-indanyl) acetate (racemic)

3.89 g of (RS) 1-hydroxy-4-indanecarbonitrile in 39 ml of pyridine is cooled to 0° C., 3.45 ml of acetic anhydride is added drop by drop, and the whole is agitated for 16 hours at 20° C. The reaction mixture is poured into 300 ml of water containing sodium chloride and extracted with isopropyl ether; the ethereal phase is washed with 2N hydrochloric acid and then with water until pH 7 is obtained. The ethereal phase is dried and brought to dryness, and the residue is taken up in 1,2-dichloroethane, and again concentrated to dryness under reduced pressure. The residue is taken up in 40 ml of hexane, agitated for one hour, filtered, and 4.46 g of expected product is recovered. M.p.=65° C.

Stage B: R(±) 1-hydroxy-4-indanecarbonitrile and its S(−) acetate 4.46 g of product obtained above, 24.4 ml of acetone and 190 ml of pH 8 buffer are agitated at 20° C. The pH is checked, namely 7.98, and 4.46 g of enzyme (PPL Sigma type II: lipase of the pancreas of a pig) is introduced. After agitation for 28 hours at 20° C., the mixture is poured into 200 ml of 2N hydrochloric acid and 200 ml of ethyl acetate, celite (clarcel) is added, with further agitation for 15 minutes. After filtering on celite, the filtrate is rinsed, decanted and extracted with ethyl acetate, and the extracts are dried and brought to dryness under reduced pressure. The residue is chromatographed on silica in a hexane-ethyl acetate mixture (7-3). 1.05 g of (R) alcohol is obtained, M.p.=98° C., [alpha]$_D$=+13°±2° (c=0.6% CHCl$_3$) and 2.96 g of acetate rich in isomer (S) is obtained. This 2.96 g of product is agitated in 16.2 ml of acetone and 120 ml of pH 8 buffer, the pH is adjusted to 8 with 2 ml of 1N hydrochloric acid and 2.96 g of enzyme is introduced in one lot, then the whole is agitated for 19 hours. The reaction mixture is poured into 150 ml of 2N hydrochloric acid and 150 ml of ethyl acetate, with agitation for 5 minutes; celite is added and agitation is continued for 15 minutes. After filtering on celite, the filtrate is rinsed, decanted and extracted with ethyl acetate. The organic phase is dried and concentrated to dryness under reduced pressure, and the residue is chromatographed in a hexane-ethyl acetate mixture (7-3). 2.22 g of S(−) 4-cyano-1-indanyl acetate and 0.49 g of (R) alcohol are obtained, M.p.=98° C.

Stage C: S(−) 1-hydroxy-4-indanecarbonitrile 2.12 g of acetate obtained above in 21 ml of alcohol at 90% are agitated together for 5 minutes, 1.36 ml of concentrated sodium hydroxide is added, with agitation for 15 minutes at 0° C. and for 15 minutes at 10° C. The reaction mixture is poured into 50 ml of water containing potassium hydrogenophosphate and extracted with methylene chloride. The organic phase is dried and brought to dryness under reduced pressure. The residue is taken up in 17 ml of hexane, agitated for one hour and filtered. The filtrate is dried at 45° C. under reduced pressure and 1.56 g of expected product is recovered, M.p.=98° C.

[alpha]$_D$= −14°±1° (c=1% CHCl$_3$).

PREPARATION 14

1-hydroxy-6-indanecarbonitrile (racemic)

Stage A: 1-oxo-6-indanecarbonitrile 2 g of 6-bromo-indanone, 10 ml of dimethylformamide and 3 g of copper cyanide are taken to reflux for 20 hours. At 20° C. the reaction mixture is poured into 40 ml of water and 30 ml of methylene chloride, agitated for 15 minutes and filtered on celite. The filtrate is decanted and re-extracted with methylene chloride. The organic phase is washed with water, dried, brought to dryness under reduced pressure and the residue is chromatographed on silica in a hexane-ethyl acetate mixture as eluant (7-3). 1.03 g of expected product is obtained, M.p.=109° C.

Stage B: 1-hydroxy-6-indanecarbonitrile (racemic)

1 g of product obtained above, 100 ml of tetrahydrofuran and 15 ml of water are cooled to 0° C.-5° C., 950 mg of potassium borohydride at 95% is added, with agitation for 10 minutes at 0° C. and for one hour at 20° C. The reaction mixture is poured into 150 ml of water containing sodium chloride; the aqueous phase is decanted and extracted with isopropyl ether; the extracts are dried and concentrated to dryness under reduced pressure. The residue is chromatographed on silica in a hexane-ethyl acetate mixture (6-4) and 980 mg of expected product is obtained.

PREPARATION 15

1-hydroxy-7-indanecarbonitrile (racemic).

The operation is carried out as in preparation 14, starting with 1.84 g of 7-bromoindanone, and 1.07 g of expected product is obtained, M.p.=73° C.

PREPARATION 16

1-hydroxy-4-indaneacetonitrile

Stage A: alpha-bromo-2-iodo toluene 22 g of 2-iodotoluene, 100 ml of carbon tetrachloride, 19.67 g of N-bromo succinimide and 1 g of benzoyl peroxide are mixed together and heated to reflux for 8 hours. After filtering, the insoluble part is rinsed with carbon tetrachloride and the filtrate is distilled off, firstly under atmospheric pressure, then under reduce pressure. The expected product is obtained, and used just as it is for the continuation of the synthesis.

Stage B: 4-iodo-1-indanol

The operation is carried out as in preparation 6, Stage B, C, D and E, starting with the product obtained above, so as to obtain the expected product, M.p.=83°-84° C.

Stage C: 4-iodo-1-trimethylsilyloxy-indane (racemic)

5.2 g of the alcohol obtained above in 100 ml of ether and 5 ml of triethylamine are brought to 0° C. and 4.1 ml of trimethyl silyl chloride is added, followed by agitating for one hour at ambient temperature. After filtering, the insoluble part is rinsed with ether and water is added to the filtrate. After decanting, extraction is carried out with ether, and the extracts are washed with water until a neutral pH is obtained, dried and evaporated to dryness. 5.9 g of crude product is obtained, used just as it is.

Stage D: 1-hydroxy-4-indaneacetic 20 ml of 1,3-dimethyl imidazolidone and 3.34 g of sodium hydride at 50% are cooled to +15° C. 7 ml of ethyl cyano acetate in 33 ml of 1,3-dimethyl imidazolidone is added over 10 minutes and agitation is carried out for one hour. 13.2 g of cuprous iodide, 11.5 g of iodized derivative obtained in stage C and 11 ml of 1,3-dimethyl imidazolidone are added to the solution obtained, which is then taken to 95° C. for 4 hours. 2.5 g of sodium hydroxide in 52 ml of water is added over 5 minutes at 90° C. to the suspension obtained, and heating is maintained at 90° C. for 2 hours. After cooling, the medium is poured into 400 ml of 2N hydrochloric acid, agitated for 30 minutes, filtered on celite, rinsed with water and with ethyl acetate. After decanting, the aqueous phase is saturated with sodium chloride and extracted with ethyl acetate. The organic phases are washed with a saturated solution of sodium bicarbonate, and with water saturated with sodium chloride, dried and brought to dryness under reduced pressure. The residue is chromatographed on silica with a dichloro difluoro ethane-ethyl acetate mixture (1-1), and 4.36 g of crude product is isolated. The latter is taken up hot in 180 ml of isopropyl ether, filtered and 1.05 g of expected product is recovered (white crystals) and 3.24 g of beige crystals is recovered, which is chromatographed again so as to obtain 1.84 g of expected product and 0.79 g of expected impure product.

| IR Spectrum in CHCl$_3$: | |
| --- | --- |
| OH presence | 3599 cm$^{-1}$ |
| CN | 2255 cm$^{-1}$, 210 cm$^{-1}$ |
| Aromatic | 1616 cm$^{-1}$, 1600 cm$^{-1}$, 1479 cm$^{-1}$ |

PREPARATION 17 ethyl alpha-cyano-1-hydroxy-4-indane acetate 6 ml of 1,3-dimethyl-2-imidazolidone and 0.99 g of sodium hydride at 50% are cooled to +15° C., 2.2 ml of ethyl cyanacetate in 10 ml of 1,3-dimethyl-2-imidazolidone is added over 5 minutes, with agitation for 40 minutes. 4.39 g of cuprous iodide, 3.62 g of 4-iodo-1-trimethylsilyloxy indane and 4 ml of 1,3-dimethyl-2-imidazolidone are added. The mixture is taken to 100° C. for 4 hours. After cooling, it is poured into 100 ml of 2N hydrochloric acid, filtered on celite, and rinsed with water; the filtrate is extracted with isopropyl ether, washed with a saturated solution of sodium bicarbonate and with water, dried and brought to dryness. The residue is chromatographed on silica in a hexane-ethyl acetate mixture (1-1) and 1.22 g of expected product is obtained.

| IR Spectrum CHCl₃: | |
|---|---|
| —OH | 3600 cm⁻¹ |
| —CN | 2255 cm⁻¹ |
| —C=O | 1746 cm⁻¹ |

PREPARATION 18

4-propyl-1-indanol (racemic)

Stage A: 4-propyl-1-indanone 1.63 g of 4-(2-propenyl)-1-indanone is dissolved in 300 ml of anhydrous ethanol and 400 mg of rhodium at 5% on active charcoal and hydrogenated at ambient temperature and ambient pressure for ¾ hour. After filtering on celite, the filtrate is washed with ethanol and evaporated to dryness, and 1.56 g of expected product is obtained.

Stage B: 4-propyl-1-indanol (racemic)

1.56 g of above product in 30 ml of ethanol is cooled to 0° C., 0.2 g of sodium borohydride is added and the mixture is left for 16 hours at ambient temperature. It is poured into 300 ml of water and extracted with ether, the extracts are dried and evaporated to dryness under reduced pressure. 1.58 g of expected product is obtained.

| IR Spectrum: | |
|---|---|
| No C=O | |
| OH 3600 cm⁻¹ | |

PREPARATION 19

4-(2-methyl-2-propenyl)-1-indanol

Stage A: 4-(2-methyl-2-propenyl)-1-indanone 9 g of (2-methyl-2-propenyl)-tributyl stannane, 5.25 g of 4-bromo indanone, 50 ml of dimethylformamide and 300 g of tetrakis phenyl phosphine palladium are heated to 125° C. under agitation for 45 minutes. After cooling, the mixture is poured into an iced solution of 7.5 g of potassium fluoride in 300 ml of water, agitated for 5 minutes and filtered on celite. The filtrate is extracted with isopropyl ether, dried and concentrated to dryness under reduced pressure. The residue is chromatographed on silica, eluting with a hexane-ethyl acetate mixture (8-2) and 4 g of expected product is recovered.

| IR Spectrum: | |
|---|---|
| C=O | 1706 cm⁻¹ |
| C=CH₂ | 1649 cm⁻¹ |
|  | 897 cm⁻¹ |
| Aromatic | 1603 cm⁻¹ |
|  | 1592 cm⁻¹ |
|  | 1482 cm⁻¹ |

PREPARATION OF THE (2-METHYL-2-PROPENYL)-TRIBUTYL STANNANE 4.7 g of magnesium turnings are mixed in 15 ml of tetrahydrofuran, 5 drops of dibromo-ethane and 1 drop of methallyl chloride are added. When the reaction has started, the mixture is taken to reflux while slowly introducing a solution containing 10 ml of methallyl chloride, 16.3 ml of tributyl-tin chloride and 50 ml of tetrahydrofuran. After 12 hours at reflux, the reaction mixture is cooled and poured under inert atmosphere into an ice solution, saturated with ammonium chloride (30 ml), then filtered on celite; the filtrate is rinsed with 30 ml of a saturated solution of sodium chloride and extracted with ethyl ether. The reunited organic phases are washed with 30 ml of a monopotassium phosphate solution, then with 30 ml of water. After drying and evaporating the solvent under reduced pressure, 18.8 g of crude product is obtained. This is distilled under 0.2 mm Hg and 17.5 g is recovered, B.p 2 mmHg 83°-93° C.

| IR Spectrum: | |
|---|---|
| —C=CH₂ | 3080 cm⁻¹ |
|  | 1627 cm⁻¹ |
| def | 864 cm⁻¹ |

Stage B: 4-(2-methyl-2-propenyl)-1-indanol 4.2 g of product obtained above in 80 ml of ethanol is cooled to 0° C., 1.350 g of sodium borohydride is added in fractions and agitation is carried out for 2 hours. The reaction mixture is poured into 150 ml of an iced solution of monopotassium phosphate and extracted with ether; the extracts are dried and the solvent is evaporated under reduced pressure. The residue is chromatographed on silica, eluting with a hexane-ethyl acetate mixture (8-2) and 3.95 g of expected product is recovered.

| IR Spectrum: | |
|---|---|
| —OH | 3600 cm⁻¹ |
| C=CH₂ | 1649 cm⁻¹ |
|  | 895 cm⁻¹ |
| Aromatic | 1600 cm⁻¹ |
|  | 1479 cm⁻¹ |

PREPARATION 20

4-(2-propenyl)-1-indanol RS and its 2-ol isomer 0.61 g of magnesium turnings in 1 ml of tetrahydrofuran is heated to 65° C., 2 drops of 1,2-dibromoethane is added and first 2 drops, then drop by drop a solution of 7 g of 4-bromo-1-trimethyl siloxy indane in 41 ml of tetrahydrofuran is added. The mixture is then taken to reflux for 2 hours and a magnesium compound is obtained titrating 0.56N. 1.7 g of methoxyallene and 0.28 g of cuprous iodide are agitated in 24 ml of ether and drop by drop 44 ml of the magnesium compound is added over 10 minutes. After 45 minutes 1 g of methoxyallene is added with further agitation for 35 minutes at 20° C. The reaction medium is poured into 150 ml of a saturated solution of ammonium chloride, 2 ml of a solution of ammonia at 20% is added and extraction is done with isopropyl ether. The ethereal phase is washed with water, then with a 0.2N solution of sodium thiosulphate and finally with water, after which it is dried and brought to dryness under reduced pressure. The oily residue obtained is taken up in 25 ml of tetrahydrofuran, 16.2 ml of a 1M solution of tetrabutylammonium fluoride in tetrahydrofuran is added in one lot and the whole is agitated for 10 minutes. The reaction medium is poured into 100 ml of water and extracted with isopropyl ether; the ethereal phase is washed with water until pH 7 is obtained, then dried and brought to dryness under reduced pressure. The residue is chromatographed on silica in a hexane-ethyl acetate mixture (7-3) and 1.56 g of expected product is recovered, M.p.=70° C.

| IR Spectrum CHCl₃: | |
|---|---|
| OH 3600 cm$^{-1}$ | |
| C≡CH ( ≡CH) | 3310 cm$^{-1}$ |
| (C≡C) | 2100 cm$^{-1}$ |
| Aromatic | 1599 cm$^{-1}$ |
| | 1478 cm$^{-1}$ |

Starting from 4-bromo-2-trimethylsiloxy indane and operating as above, 2,3-dihydro-4-(2-propenyl)-2H-inden-2-ol is obtained.

PREPARATION 21

4-(2-chloro-2-propenyl)-1-indanol (racemic)

Stage A: 4-(tributyl stannyl)-1-indanone 1.5 g of 4-iodo-indane-1-one is dissolved in 15 ml of dimethylformamide and 10 ml of hexamethyl phosphorotriamide, 4.35 ml of hexabutyl di-tin and 30 mg of dichloro diacetonitrile-palladium are added and agitation is carried out for 16 hours at ambient temperature. The reaction mixture is poured into 200 ml of an aqueous solution of potassium fluoride, agitated and filtered on celite; after rinsing with ethyl acetate, the filtrate is extracted with isopropyl ether, the organic phases are dried and concentrated to dryness. The residue is chromatographed on silica with a hexane-isopropyl ether mixture (9-1) and 1.91 g of expected product is isolated.

| IR Spectrum (CHCl₃): |
|---|
| C=O 1704 cm$^{-1}$ |

Stage B: 4-(2-chloro-2-propenyl)-1-indanone 12 g of product obtained above, 5.25 ml of 2,3-dichloro-1-propene, 120 ml of toluene and 150 mg of dichloro-diacetonitrile-palladium are heated to 100° C. and agitated for 20 minutes at 100° C. After cooling, the reaction medium is poured into 150 ml of an aqueous solution of 10 g of potassium fluoride, 100 ml of ethyl acetate is added and vigorous agitation is carried out for 10 minutes. After filtering on celite, the filtrate is rinsed abundantly with ethyl acetate, then decanted and re-extracted with ethyl acetate. The reunited organic phases are dried and evaporated under reduced pressure. The residue is chromatographed on silica, eluting with a hexane-ethyl acetate mixture (8-2), and 2.83 g of expected product is recovered.

| IR Spectrum: | |
|---|---|
| C—O | 1708 cm$^{1}$ |
| \C=CH₂/ | 1635 cm$^{-1}$ |
| | 889 cm$^{-1}$ |
| Aromatic | 1607 cm$^{-1}$ |
| | 1592 cm$^{-1}$ |

| -continued | |
|---|---|
| IR Spectrum: | |
| | 1482 cm$^{-1}$ |

Stage C: 4-(2-chloro-2-propenyl)-1-indanol (racemic)

2.8 g of product obtained above in 60 ml of ethanol at 90° C. is cooled to 0° C., 250 mg of sodium borohydride is introduced with agitation for 75 minutes at 0° C. 250 mg of borohydride is added at 20° C. and the whole is poured into an iced solution of potassium mono-potassium phosphate and extracted with ether; the organic phases are dried and concentrated to dryness under reduced pressure. The residue is chromatographed on silica, eluting with a hexane-ethyl acetate mixture (3-1) and 1.67 g of expected product is recovered.

| IR Spectrum: | |
|---|---|
| OH | 3600 cm$^{-1}$ |
| \C=CH₂/ | 1635 cm$^{-1}$ |
| | 890 cm$^{-1}$ |
| Aromatic | 1602 cm$^{-1}$ |
| | 1479 cm$^{-1}$ |

PREPARATION 22

R (−) 4-(2-propenyl)-1-indanol and its S (+) isomer

Stage A: 4-bromo-1-indanyl acetate 3.0 g of 4-bromo-1-indanol (RS) in 30 ml of pyridine is cooled to 0° C., 2 ml of acetic anhydride is introduced slowly with agitation for 17 hours at ambient temperature. It is then poured into 100 ml of water and 100 ml of isopropyl ether and decanted; the organic phase is washed with water, dried and concentrated to dryness. The residue is taken up in 1,2-dichloro ethane in order to eliminate the pyridine by azeotropy. 3.9 g of expected product is obtained.

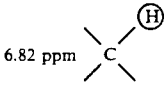

| NMR Spectrum (CDCl₃): |
|---|
| 2.02 ppm CH₃ |
| 2.68 ppm φ CH₂—CH₂ |
| 6.82 ppm (structure shown) |
| 7.22 ppm (m) aromatics |

Stage B: R (+) 4-bromo-1-indanol 4.49 g of product obtained above in 19 ml of acetone and 180 ml of a pH 8 buffer solution is adjusted to pH 8, by the addition of N hydrochloric acid. 4.5 g of lipase of the pancreas of a pig, Sigma type II is introduced in one lot. After 5 hours the reaction mixture is poured into 200 ml of 2N hydrochloric acid and 200 ml of methylene chloride, celite is added and the whole is agitated for half an hour at ambient temperature. After filtering on celite, the filtrate is decanted and the aqueous phase is extracted with methylene chloride. The organic phases are reunited, dried and concentrated to dryness under reduced pressure. The residue is chromatographed on silica in a hexane-ethyl acetate mixture (8-2) and 2.38 g of acetate rich in isomer "S" and 1.48 g of expected "R" alcohol are obtained, M.p.=84° C.

[alpha]$_D$+2°±0.5° c=1% CHCl$_3$

Stage C: (S) 4-bromo-1-indanyl acetate

The operation is carried out as above, starting with 2.28 g of S mixture obtained above; the residue is chromatographed on silica in a hexane-isopropyl ether mixture (9-1), then a hexane-ethyl acetate mixture, and firstly 1.85 g of expected S acetate is obtained, then 0.22 g of alcohol crystals is obtained (R+S mixture).

Stage D: S (−) 4-bromo-1-indanol 1.85 g of S acetate obtained above is dissolved in 15 ml of 90% alcohol, with agitation; 0.53 g of potassium hydroxide in pastille form is introduced little by little, maintaining agitation at ambient temperature for one hour. The mixture is poured into 150 ml of water and 100 ml of methylene chloride. After decanting, the aqueous phase is extracted with methylene chloride; the reunited organic phases are washed with water, dried and concentrated to dryness under reduced pressure. 1.53 g of expected product is obtained, M.p.=81° C.

[alpha]$_D$ −8°±1° (c=1% CHCl$_3$)

Stage E: S(+) 4-(2-propenyl)-1-indanol 1.48 g of alcohol obtained in Stage D, 15 ml of dimethylformamide, 2.3 ml of tributylallyl-stannane and 80 mg of tetrakis triphenyl phosphine-palladium are taken to 120° C. for 2 hours. The reaction mixture is poured on to 1 g of potassium fluoride in 100 ml of water and agitated for 15 minutes, filtered on celite, and the filtrate is rinsed with isopropyl ether and decanted. The organic phase is washed with water, dried and concentrated to dryness under reduced pressure. The residue is chromatographed in a hexane-ethyl acetate mixture (8-2), and 0.84 g of expected product and 0.27 g of mixture are obtained.

[alpha]$_D$ +95°±2° (c=0.6% CHCl$_3$)

Stage F: R (−) 4-(2-propenyl)-1-indanol

The operation is carried out as in Stage E, starting with 1.37 g of R alcohol obtained in Stage B, and 1.02 g of expected product is obtained.

[alpha]$_D$ −12.5°±2° (c=0.5° CHCl$_3$).

A homogeneous mixture is made of:

| Example 68: preparation of a soluble concentrate A homogeneous mixture is made of: | |
|---|---|
| Product of Example 1 | 0.25 g |
| Piperonyl butoxide | 1.00 g |
| Tween 80 | 0.25 g |
| Topanol A | 0.1 g |
| Water | 98.4 g |
| Example 69: preparation of an emulsifiable concentrate The following intimately mixed: | |
| Product of Example 2 | 0.015 g |
| Piperonyl butoxide | 0.5 g |
| Topanol A | 0.1 g |
| Tween 80 | 3.5 g |
| Xylene | 95.885 g |
| Example 70: preparation of an emulsifiable concentrate A homogeneous mixture is made of: | |
| Product of Example 54 | 1.5 g |
| Tween 80 | 20.0 g |
| Topanol A | 0.1 g |
| Xylene | 78.4 g |
| Example 71: preparation of a fumigant composition The following are homogeneously mixed: | |
| Product of Example 56 | 0.25 g |
| Tabu powder | 25.00 g |
| Cedar leaf powder | 40.00 g |
| Pine sawdust | 33.75 g |
| Brilliant green | 0.50 g |
| p-nitrophenol | 0.50 g |

BIOLOGICAL STUDY

A) Study of the Knock-Down Effect on Household Flies

The insects tested are 4-day old, female household flies. The operation is carried out by direct spraying at the concentration indicated, in a Kearns and March chamber, using as a solvent a mixture of acetone (5%) and Isopar L (petroleum solvent) (quantity of solvent used: 2 ml per second). 50 insects per treatment are used. Checks are made every minute for 10 minutes, then at 15 minutes, and the KT 50 is determined by the usual methods.

The experimental results obtained are summarized in the following table:

| Compounds of Example | KT50 in mn |
|---|---|
| 1 | 5.5 at 1 g/l |
| 2 | 3.7 at 1 g/l |
| 6 | 2.5 at 1 g/l |
| 32 | 3.5 at 0.1 g/l |
| 35 | 2.4 at 1 g/l |
| 54 | 3.12 at 0.1 g/l |
| 56 | 2.7 at 0.1 g/l |

Activity on *Tetranychus urticae*. Adulticide test

Bean plants having two cotyledonary leaves are used. These plants are treated with an acetone solution of the product using a Fisher gun. After drying, 25 females of the acarid *Tetranychus urticae* per leaf are placed on the plant, that is 50 individuals per experimental dose per plant. The check for effectiveness is carried out after 80 hours of contact. The LC 50 is measured in mg/hl.

| Example | LC 50 |
|---|---|
| 1 | 27.9 |
| 2 | 95 |
| 8 | 26.4 |
| 6 | 90 |
| 7 | 25 |
| 35 | 36.9 |
| 57 | 20 |

Conclusion: The products of the invention are endowed with a remarkable acaricide effect on *Tetranychus urticae*.

B) Study of the Lethal Effect of the Compounds of the Invention on Various Insects Study of the Lethal Effect on the Household Fly The insects tested are 4- to 5-day old female household flies. The operation is carried out by topical application of 1 μl of acetone solution on the dorsal thorax of the insects using an Arnold micromanipulator. 50 individuals per treatment are used. The mortality check is carried out 24 hours after treatment.

The results obtained, expressed in LD 50 or dose (in nanograms) per individual necessary to kill 50% of the insects, are the following:

| Compounds of Example | LD in ng/insect |
|---|---|
| 2 | 4.2 |
| 6 | 3.9 |
| 54 | 1.7 |

C) Study of the Lethal Effect on a Cockroach

The tests are carried out by contact on a film on glass, by depositing with a pipette acetone solutions of various concentrations on the bottom of a glass Petri dish, the edges of which are previously talcum powdered so as to avoid the escape of the insects. The lethal concentration 50 (LC 50) is determined.

The experimental results obtained are summarized in the following table:

| Compounds of Example | LC 50 in mg/m2 |
|---|---|
| 1 | 0.29 |
| 5 | 0.24 |

We claim:

1. A compound selected from the group consisting of all possible isomers and mixtures of a compound of the formula

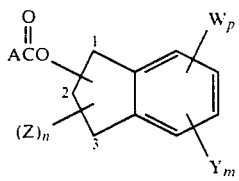

in which

is fixed in position 1, A is

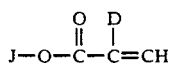

wherein D is selected from the group consisting of hydrogen, halogen and alkoxy of 1 to 8 carbon atoms, J is selected from the group consisting of alkyl of 1 to 8 carbon atoms, alkenyl and alkynyl of 2 to 8 carbon atoms, cycloalkyl of 3 to 8 carbon atoms and carbocyclic aryl of 6 to 14 carbon atoms, all optionally substituted with at least one functional group consisting of halogen, cyano, alkoxy of 1 to 8 carbon atoms, —OH,

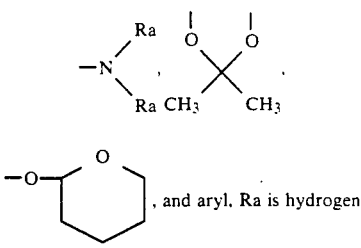, and aryl, Ra is hydrogen or alkyl of 1 to 8 carbon atoms, Z is in 2- or 3-position and is selected from the group consisting of hydrogen, halogen, alkyl of 1 to 8 carbon atoms, alkenyl and alkynyl of 2 to 8 carbon atoms, cycloalkyl of 3 to 8 carbon atoms, carbocyclic aryl of 6 to 14 carbon atoms, and =O, n is an integer from 1 to 3, Y is in position 4 of the aromatic ring and is —CH$_2$—CH=CH$_2$, m is 1, W is hydrogen p is 1 or 2.

2. A compound of formula (I) as defined in claim 1, in which D represents a hydrogen atom, and J represents a saturated or unsaturated linear, branched or cyclic alkyl radical containing up to 4 carbon atoms, optionally substituted by one or more halogen atoms.

3. A compound of formula (I) as defined in claim 1, in which D represents a fluorine atom, and J is a saturated or unsaturated linear, branched or cyclic alkyl radical containing up to 4 carbon atoms, optionally substituted by one or more halogen atoms.

4. A compound of formula (I) as defined in claim 1, in which Z represents a hydrogen or fluorine atom.

5. A compound of claim 1 selected from the group consisting of 4-(2-propenyl)-1-indenyl-[1R-(α-(RS*)),3α(Z)]-3-[3-(1,1-dimethylethoxy)-3-oxo-1-propenyl]-2,2-dimethylcyclopropane carboxylate, 4-(2-propenyl)-1-indenyl-[1R-[1α-(RS*),3α(E)]-3-[2-fluoro-3-ethoxy-3-oxo-1-propenyl]-2,2-dimethyl-cyclopropane carboxylate and 4-(2-propenyl)-1-indenyl [1R-[1α-(RS*),3α(E)]]-3-[3-(3-ethoxy-2-fluoro-3-oxo-1-propenyl)]-2,2-dimethyl-cyclopropane carboxylate.

6. A composition intended for animal fodder, characterized in that it contains as active principle an acaracidally effective amount of a compound defined in claim 1.

7. An insecticidal composition comprising an insecticidally effective amount of a compound of claim 1 and an inert carrier.

8. A method of combatting insects comprising contacting insects with an insecticidally effective amount of a compound of claim 1.

9. A method of combatting nematodes comprising contacting nematodes with a nematoically effective amount of a compound of claim 1.

10. A method of combatting acariens comprising contacting acariens with an acaricidally effective amount of a compound of claim 1.

* * * * *